(12) United States Patent
Raemdonck et al.

(10) Patent No.: US 11,033,572 B2
(45) Date of Patent: Jun. 15, 2021

(54) MOLECULAR ADJUVANTS FOR ENHANCED CYTOSOLIC DELIVERY OF ACTIVE AGENTS

(71) Applicant: Universiteit Gent, Ghent (BE)

(72) Inventors: Koen Raemdonck, Ghent (BE); Stefaan De Smedt, Mariakerke (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 16/479,014

(22) PCT Filed: Jan. 18, 2018

(86) PCT No.: PCT/EP2018/051220
§ 371 (c)(1),
(2) Date: Jul. 18, 2019

(87) PCT Pub. No.: WO2018/134310
PCT Pub. Date: Jul. 26, 2018

(65) Prior Publication Data
US 2019/0328768 A1 Oct. 31, 2019

(30) Foreign Application Priority Data
Jan. 19, 2017 (EP) .................................... 17152264

(51) Int. Cl.
| | | |
|---|---|---|
| C07H 21/04 | (2006.01) |
| A61K 31/713 | (2006.01) |
| A61K 9/06 | (2006.01) |
| A61K 9/51 | (2006.01) |
| A61K 31/137 | (2006.01) |
| A61K 31/404 | (2006.01) |
| A61K 31/4545 | (2006.01) |
| A61K 31/4704 | (2006.01) |
| A61K 39/39 | (2006.01) |
| A61K 47/36 | (2006.01) |
| A61K 45/06 | (2006.01) |

(52) U.S. Cl.
CPC .............. *A61K 31/713* (2013.01); *A61K 9/06* (2013.01); *A61K 9/513* (2013.01); *A61K 31/137* (2013.01); *A61K 31/404* (2013.01); *A61K 31/4545* (2013.01); *A61K 31/4704* (2013.01); *A61K 39/39* (2013.01); *A61K 47/36* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2008/0194540 A1 | 8/2008 | Neukamm et al. | |
| 2016/0145628 A1* | 5/2016 | Yerushalmi | C12N 15/1138 514/44 A |
| 2016/0317676 A1 | 11/2016 | Hope et al. | |

FOREIGN PATENT DOCUMENTS

| | | |
|---|---|---|
| WO | WO9602655 A1 | 2/1996 |
| WO | WO2007040469 A2 | 4/2007 |
| WO | WO2009126933 A2 | 10/2009 |
| WO | WO2011161075 A1 | 12/2011 |
| WO | WO2017034991 A1 | 3/2017 |

OTHER PUBLICATIONS

Soni et al. ("Nanogels as potential nanomedicine carrier for treatment of cancer: A mini review of the state of the art." Saudi Pharmaceutical Journal 24.2 (2016): 133-139).*
Aboud et al., "Development, Optimization, and Evaluation of Carvedilol-Loaded Solid Lipid Nanoparticles for Intranasal Drug Delivery", AAPS PharmSciTech, Springer US, New York, vol. 17, No. 6, 2016, pp. 1353-1365.
Aits et al., "Methods for the quantification of lysosomal membrane permeabilization: A hallmark of lysosomal cell death", Methods in Cell Biology, vol. 126, 2015, pp. 261-285.
De Backer et al., "The Influence of Natural Pulmonary Surfactant on the Efficacy of SiRNA Loaded Destran Nanogels", Nanomedicine (London), vol. 8, 2013, pp. 1625-1638.
Funk et al., "Cationic Amphiphilic Drugs Cause a Marked Expansion of Apparent Lysosomal Volume: Implications for an Intracellular Distribution-Based Drug Interaction", Molecular Pharmaceutics, vol. 9, 2012, pp. 1384-1395.
Hardie et al., "Simultaneous cytosolic delivery of a chemotherapeutic and siRNA using nanoparticle-stabilized nanocapsules", Nanotechnology, IOP, Bristol, GB, vol. 27, No. 37, 2016, p. 374001.
Jun-Ichiro Jo et al., "Preparation of Cationized Polysaccharides as Gene Transfection Carrier for Bone Marrow-Derived Mesenchymal Stem Cells", Journal of Biomaterials Science, Polymer Edition, vol. 21, No. 2, 2010 pp. 185-204.
Kirkegaard et al., "Hsp70 stabilizes lysosomes and reverts Niemann-Pick disease-associated lysosomal pathology", Nature, vol. 463, 2010, pp. 549-553.
Kornhuber et al., "Functional Inhibitors of Acid Sphingomyelinase (FIASMAs): A Novel Pharmacological Group of Drugs with Broad Clinical Applications", Cellular Physiology and Biochemistry, vol. 26, 2010, pp. 9-20.
Kornhuber et al., "Identification of New Functional Inhibitors of Acid Sphingomyelinase Using a Structure-Property-Activity Relation Model", J. Med Chem., vol. 51, 2008, pp. 219-237.
Petersen et al., "Transformation-Associated Changes in Sphingolipid Metabolism Sensitize Cells to Lysosomal Cell Death Induced by Inhibitors of Acid Sphingomyelinase", Cancer Cell, vol. 24, 2013, pp. 379-393.
Rehman et al., "Mechanism of Polyplex—and Lipoplex-Mediated Delivery of Nucleic Acids: Real-Time Visualization of Transient Membrane Destabilization without Endosomal Lysis", ACS Nano, vol. 7, No. 5, 2013, pp. 3767-3777.
Shoemaker et al., "Multiple Cationic Amphiphiles Induce a Niemann-Pick C Phenotype and Inhibit Ebola Virus Entry and Infection", PLOS One, vol. 8, Issue 2, e-56265, 2013, pp. 1-13.

(Continued)

*Primary Examiner* — Kimberly Chong
(74) *Attorney, Agent, or Firm* — Dinsmore & Shohl, LLP

(57) ABSTRACT

The present invention relates to a method and compositions for optimized intracellular delivery of active agents, in particular nucleic acids, using a specific class of adjuvants. The method and compositions of the invention enhance cytosolic release of the agents and can be used for the treatment of various disorders.

12 Claims, 12 Drawing Sheets

Specification includes a Sequence Listing.

(56) References Cited

OTHER PUBLICATIONS

Te Vruchte et al., "Relative acidic compartment volume as a lysosomal storage disorder-associated biomarker", The Journal of Clinical Investigation, vol. 124, No. 3, 2014, pp. 1320-1328.
Wishart et al., "DrugBank: a comprehensive resource for in silico drug discovery and exploration", Nucleic Acids Research, vol. 34, Database issue doi:10.1093/nar/gkj067, 2006, pp. D668-D672.
International Search Report and Written Opinion, completed Mar. 20, 2018, pertaining to PCT/EP2018/051220, filed Jan. 18, 2018.
Extended European Search Report, completed Jun. 26, 2017, pertaining to EP17152264, filed Jan. 19, 2017.
Schroeder et. al., "Chloroquine and hydroxychloroquine binding to melanin: Some possible consequences for pathologies", School of Pharmacy and Medical Sciences, Australia, 2014, pp. 963-968.

\* cited by examiner

Fig. 2 - Continued
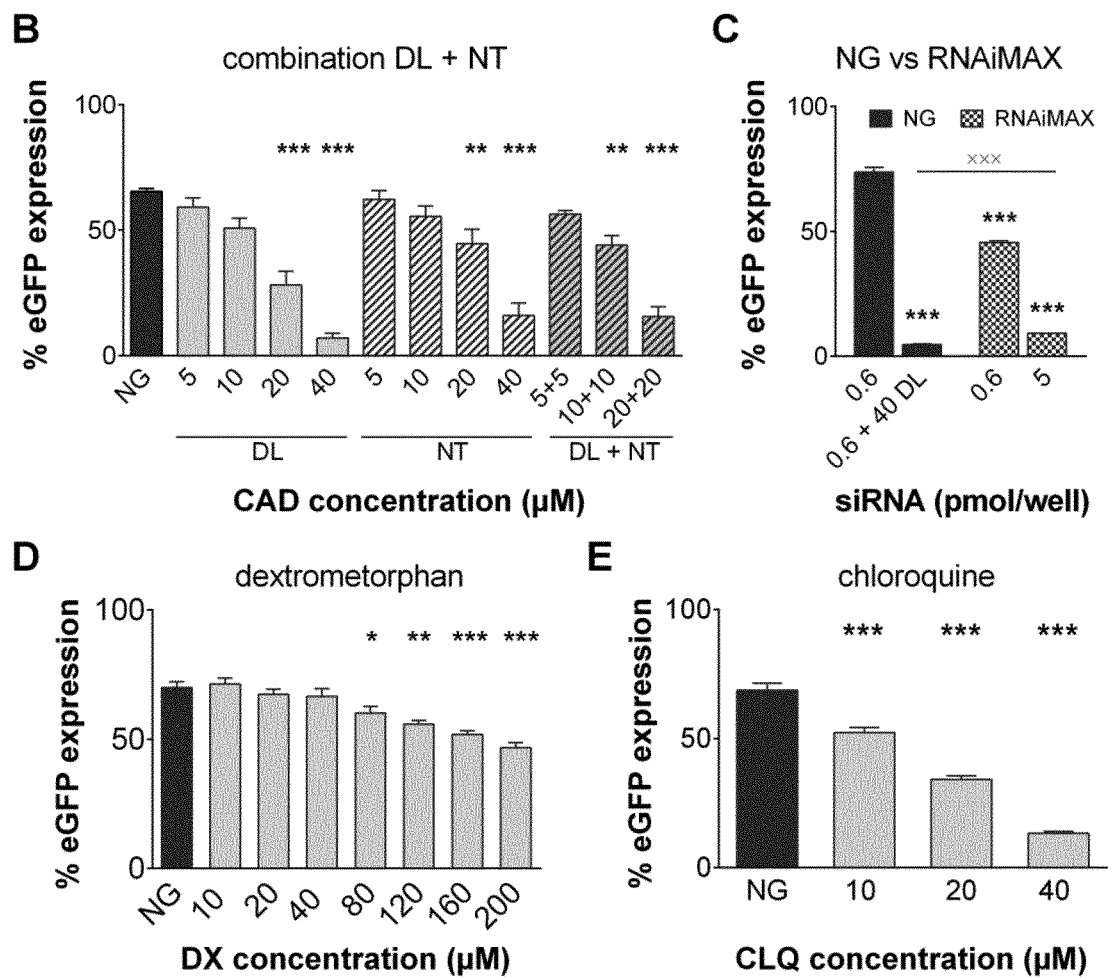
Fig. 3
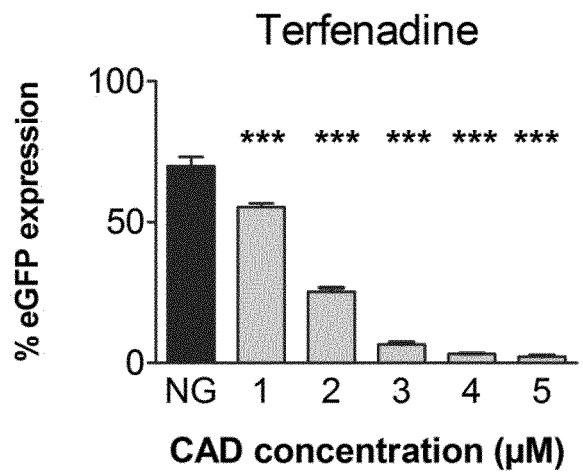

A

B

C

A

| µg mRNA | Size (nm) | ζ-potential (mV) |
|---|---|---|
| 0 | 196.2 ± 1.2 | 23.2 ± 0.1 |
| 0.1 | 196.7 ± 0.8 | 22.7 ± 0.8 |
| 0.25 | 195.5 ± 0.7 | 22.3 ± 0.7 |
| 0.5 | 195.7 ± 2.4 | 22.9 ± 0.6 |

B

C

D

E

SEQUENCE LISTING

<160> NUMBER OF SEQ ID NOS: 16

<210> SEQ ID NO 1
<211> LENGTH: 21
<212> TYPE: RNA
<213> ORGANISM: Artificial Sequence
<220> FEATURE:
<223> OTHER INFORMATION: siRNA - Sense

<400> SEQUENCE: 1
ugcgcuacga ucgacgaugt t                                              21

<210> SEQ ID NO 2
<211> LENGTH: 21
<212> TYPE: RNA
<213> ORGANISM: Artificial Sequence
<220> FEATURE:
<223> OTHER INFORMATION: siRNA - Antisense

<400> SEQUENCE: 2
caucgucgau cguagcgcat t                                              21

<210> SEQ ID NO 3
<211> LENGTH: 21
<212> TYPE: RNA
<213> ORGANISM: Artificial Sequence
<220> FEATURE:
<223> OTHER INFORMATION: siRNA - Sense

<400> SEQUENCE: 3
ugcgcuacga ucgacgaugt t                                              21

<210> SEQ ID NO 4
<211> LENGTH: 21
<212> TYPE: RNA
<213> ORGANISM: Artificial Sequence
<220> FEATURE:
<223> OTHER INFORMATION: siRNA - Antisense

<400> SEQUENCE: 4
caucgucgau cguagcgcat t                                              21

<210> SEQ ID NO 5
<211> LENGTH: 21
<212> TYPE: RNA
<213> ORGANISM: Artificial Sequence
<220> FEATURE:
<223> OTHER INFORMATION: siRNA - Sense

<400> SEQUENCE: 5
uagcgacuaa acacaucaau u                                              21

<210> SEQ ID NO 6
<211> LENGTH: 21
<212> TYPE: RNA
<213> ORGANISM: Artificial Sequence
<220> FEATURE:
<223> OTHER INFORMATION: siRNA - Antisense

<400> SEQUENCE: 6
uugauguguu uagucgcuau u                                              21

<210> SEQ ID NO 7
<211> LENGTH: 21
<212> TYPE: RNA
<213> ORGANISM: Artificial Sequence

```
<220> FEATURE:
<223> OTHER INFORMATION: siRNA - Sense

<400> SEQUENCE: 7
caagcugacc cugaaguuct t                                               21

<210> SEQ ID NO 8
<211> LENGTH: 21
<212> TYPE: RNA
<213> ORGANISM: Artificial Sequence
<220> FEATURE:
<223> OTHER INFORMATION: siRNA - Antisense

<400> SEQUENCE: 8
gaacuucagg gucagcuugt t                                               21

<210> SEQ ID NO 9
<211> LENGTH: 21
<212> TYPE: RNA
<213> ORGANISM: Artificial Sequence
<220> FEATURE:
<223> OTHER INFORMATION: siRNA - Sense

<400> SEQUENCE: 9
caagcugacc cugaaguucu u                                               21

<210> SEQ ID NO 10
<211> LENGTH: 21
<212> TYPE: RNA
<213> ORGANISM: Artificial Sequence
<220> FEATURE:
<223> OTHER INFORMATION: siRNA - Antisense

<400> SEQUENCE: 10
gaacuucagg gucagcuugu u                                               21

<210> SEQ ID NO 11
<211> LENGTH: 21
<212> TYPE: RNA
<213> ORGANISM: Artificial Sequence
<220> FEATURE:
<223> OTHER INFORMATION: siRNA - Sense

<400> SEQUENCE: 11
caaccaaagu cgaauaugau u                                               21

<210> SEQ ID NO 12
<211> LENGTH: 21
<212> TYPE: RNA
<213> ORGANISM: Artificial Sequence
<220> FEATURE:
<223> OTHER INFORMATION: siRNA - Antisense

<400> SEQUENCE: 12
ucauauucga cuuugguugu u                                               21

<210> SEQ ID NO 13
<211> LENGTH: 23
<212> TYPE: RNA
<213> ORGANISM: Artificial Sequence
<220> FEATURE:
<223> OTHER INFORMATION: DsiRNA - Sense

<400> SEQUENCE: 13
acccugaagu ucaucugcac cac                                             23
```

```
<210> SEQ ID NO 14
<211> LENGTH: 27
<212> TYPE: RNA
<213> ORGANISM: Artificial Sequence
<220> FEATURE:
<223> OTHER INFORMATION: DsiRNA - Antisense

<400> SEQUENCE: 14
acugggacuu caaguagacg ugguggc                                          27

<210> SEQ ID NO 15
<211> LENGTH: 25
<212> TYPE: RNA
<213> ORGANISM: Artificial Sequence
<220> FEATURE:
<223> OTHER INFORMATION: DsiRNA - Sense

<400> SEQUENCE: 15
gguuccugga acaauugcuu uuaca                                            25

<210> SEQ ID NO 16
<211> LENGTH: 27
<212> TYPE: RNA
<213> ORGANISM: Artificial Sequence
<220> FEATURE:
<223> OTHER INFORMATION: DsiRNA - Antisense

<400> SEQUENCE: 16
gaccaaggac cuuguuaacg aaaaugu                                          27
```

MOLECULAR ADJUVANTS FOR ENHANCED CYTOSOLIC DELIVERY OF ACTIVE AGENTS

FIELD OF THE INVENTION

The present invention relates to a method and compositions for optimized intracellular delivery of active agents, in particular nucleic acids, using a specific class of adjuvants. The method and compositions of the invention enhance cytosolic release of the agents and can be used for the treatment of various disorders.

BACKGROUND TO THE INVENTION

A major bottleneck impeding the widespread use of many therapeutics with an intracellular target is the lack of suitable delivery platforms that are able to surmount the numerous biological barriers en route to their intracellular site-of-action. To this end, such therapeutics are typically formulated into nanometer-sized drug carriers.

However, the development and optimization of efficient delivery systems has to address several issues when the active substance is administered in vivo, either via topical or systemic administration. Such issues include a) toxicity issues, b) issues with respect to "extracellular barriers" such as degradation of the active agent, unwanted opsonization of particles by serum components, rapid clearance (e.g. by the mononuclear phagocyte system) and accumulation in non-target tissues, as well as c) issues with respect to the "cellular barriers" for their intracellular delivery such as low endocytic uptake in the target cells, inadequate release of molecules in the active cellular compartment (e.g. cytosol), and lack of nuclear targeting (e.g. required for gene therapy).

In the prior art, active agents have been encapsulated into nanocarriers, e.g. liposomes, micelles and polymeric nanoparticles, in which they are protected from degradation in the extracellular environment. Alternatively, such carriers may include targeting moieties such as antibodies, polypeptides, nucleic acids (i.e. aptamers) and other substances to direct the active agents to the selected target cells. The prior art also employs a variety of chemistries for covalent coupling of nucleic acids and other active agents to molecular carriers that include polymers such as poly(ethylene glycol) (PEG) or other molecules aiming to modulate pharmacokinetics and biodistribution, including targeting ligands (e.g. N-acetylgalactosamine, antibodies, aptamers) or lipophilic molecules such as cholesterol linked to hydrophilic nucleic acids (e.g. small interfering RNA (siRNA)) to alter biodistribution and enhance cellular uptake.

To be effective, most active agents with an intracellular target have to be taken up by the cells and have to reach the cytoplasm and/or nucleus. As mentioned above, delivery of membrane-impermeable active agents, such as nucleic acids, requires formulation into appropriate delivery systems such as micro- and nanoparticles. The latter are typically taken up by cells through endocytosis. However, endocytosis sequesters the particles in endosomes and endo-lysosomes from where the active agents are unable to escape, thereby greatly reducing their therapeutic potential. For example, when an RNA interference (RNAi)-effector, such as siRNA, is enclosed in a micro- or nanocarrier, uptake generally occurs through endo-cytosis upon which the bulk of the cargo remains inactive within the endo-lysosomal compartment and is typically degraded.

Prior art discloses the use of cationic polymers such as polyethylenimine (PEI) (WO199602655). However, the use of PEI often is limited by its cytotoxicity and so far has not been approved for use in humans. Also the use of cationic lipids, e.g. as part of cationic liposomes, is described (US20160317676) although they often demonstrate identical shortcomings as documented for their polymeric counterparts. Moreover, it has been described in the literature for state-of-the-art lipid nanocarriers that only a limited fraction of up to 1-2% of the encapsulated siRNA is able to escape from the endosomal compartment and reach its site of action in the cytoplasm. Prior art also discloses small molecules improving endocytosis for use in pharmaceutical compositions (e.g. US20080194540; WO2011161075). Further, "endosomolytic" agents such as chloroquine (WO2007040469; WO2009126933) are known to enhance the transfection of nucleic acids by facilitating their escape from endosomes into the cytoplasm of cultured cells. However, as for polycationic carriers, the use of chloroquine is limited by its systemic toxicity. Various other small molecule enhancers of nucleic acid delivery have recently been identified although most have a specific mode of action and solely apply to a specific type of oligonucleotide or nanocarrier.

In order to avoid lysosomal degradation of the nanocarrier and its cargo, a general consensus exists that endosomal escape should occur as soon as possible upon cellular internalization. Consequently, the time frame in which such endosomal escape strategies can be of benefit is limited, as nanocarriers can undergo fast trafficking to the lysosomes (i.e. within the hour following endocytosis). Moreover, it is believed that membrane-destabilizing agents to induce endosomal escape should ideally avoid acting on lysosomes, as lysosomal membrane permeabilization (LMP) is considered a hallmark of lysosomal cell death (Aits et al., Methods Cell Biol., 2015).

In the present invention, we have identified novel molecular adjuvants that can safely enhance the intracellular delivery of an active agent, through inducing a higher efficiency of endosomal escape, more in particular lysosomal escape.

SUMMARY OF THE INVENTION

The present invention relates to a method, compositions, kits, combinations and uses thereof, for optimized cytosolic delivery of active agents. The composition, kit or combination comprises a nanocarrier, an active agent and at least one adjuvant, in particular a cationic amphiphilic compound, more in particular a cationic amphiphilic drug (CAD) or salts thereof. In one embodiment, the CAD is characterized by a log P value of at least 3 and the CAD comprises one or more basic amines, the conjugated acid of no more than one, and more specific only one of said amines having a pKa of at least 5.

In a further embodiment, the adjuvant is a cationic amphiphilic drug (CAD) and a functional inhibitor of acid sphingomyelinase (FIASMA) and/or is capable of inducing lysosomal membrane permeabilization (LMP) in a cell.

In another embodiment, the nanocarrier is a polymeric nanoparticle, in particular a dextran nanogel and is coupled to or comprises an active agent. The method, composition, kit or combination of the present invention is particularly useful for delivering an agent, such as a membrane-impermeable agent, into the cytosol of a cell by release of the agent from the lysosomal compartment. The agent can be a diagnostic or therapeutic agent, in particular a nucleic acid, more in particular a small interfering RNA (siRNA).

In a further embodiment, the composition, kit or combination of the present invention is used as a medicament, in particular in a method of delivering an agent into the cytosol of a cell by in vitro, ex vivo or in vivo application. The nanocarrier coupled to or comprising an active agent is administered to a cell or subject prior, concurrent or after the administration of said at least one adjuvant to said cell or subject.

BRIEF DESCRIPTION OF THE DRAWINGS

With specific reference to the figures, it is to be noted that the particulars shown are by way of example and for purposes of illustrative discussion of the different embodiments of the present invention. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings make it apparent to those skilled in the art how the several forms of the invention may be embodied in practice.

FIG. 3. % eGFP expression in H1299_eGFP cells following siNG transfection alone or followed by a sequential adjuvant treatment with 1, 2, 3, 4 or 5 μM terfenadine. All terfenadine concentrations significantly reduce eGFP expression compared to the siNGs alone. Data are represented as the mean±the standard error of the mean (SEM) for 3 technical replicates within a single biological replicate and statistical significance with respect to the siNGs is indicated when appropriate (*** $p<0.005$).

DETAILED DESCRIPTION OF THE INVENTION

Figure 1:
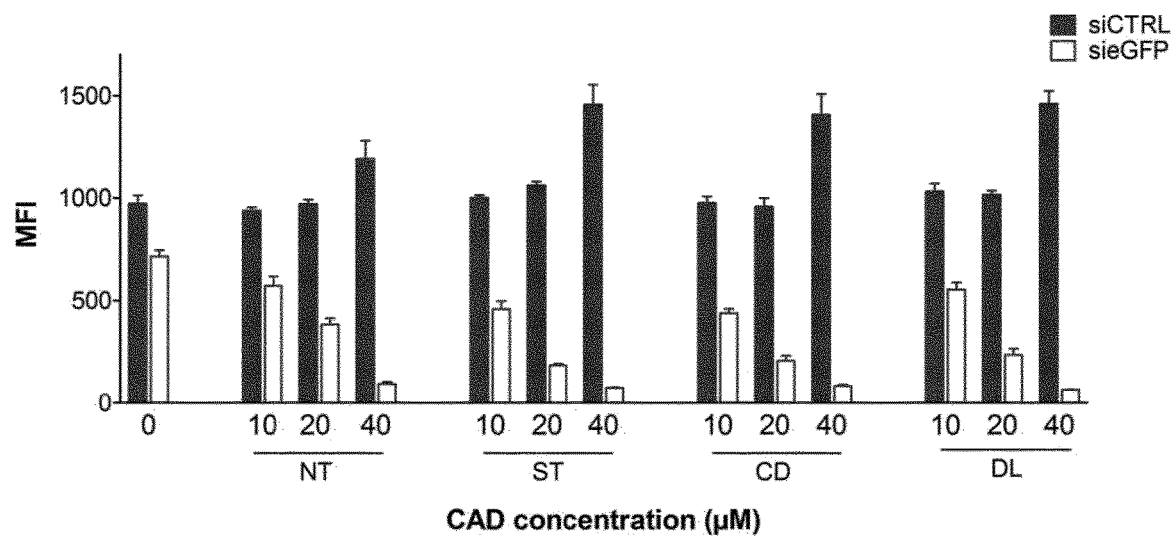
FIG. 1. The eGFP mean fluorescence intensity (MFI) for the H1299_eGFP cells transfected with siCTRL-loaded NGs (black) and NGs complexed with siEGFP (grey) followed by adjuvant treatment with 10, 20 or 40 μM nortriptyline (NT), salmeterol (ST), carvedilol (CD) or desloratadine (DL). This graph is a representative graph for four independent experiments.

The present invention will now be further described. In the following passages, different aspects of the invention are defined in more detail. Each aspect so defined may be combined with any other aspect or aspects unless clearly indicated to the contrary. As used in the specification and the appended claims, the singular forms "a", "an", and "the" include plural referents unless the context clearly dictates otherwise. By way of example, "a compound" means one compound or more than one compound. Throughout the description and claims of this specification the word "comprise" and other forms of the word, such as "comprising" and "comprises," means including but not limited to, and is not intended to exclude, for example, other additives, components, integers, or steps. The terms described above and others used in the specification are well understood to those in the art. All references, and teachings specifically referred to, cited in the present specification are hereby incorporated by reference in their entirety.

The current invention is directed to molecular adjuvants that can be used to enhance or facilitate delivery of therapeutic, biologically active or diagnostic agents into cells, more in particular for the cellular delivery of membrane-impermeable molecules in general, both macromolecular compounds but small molecules as well. Macromolecular compounds may include peptides, proteins, nucleic acids, oligosaccharides and polysaccharides.

In one embodiment, cationic amphiphilic compounds, including cationic amphiphilic drugs (CADs) or salts thereof, are applied as small molecular adjuvants prior to, together with or sequentially to transfection with drug-loaded nanomedicines. CADs are a very diverse class of small molecular pharmacological agents that are structurally characterized by a hydrophobic group (e.g. including aliphatic chains or aromatic rings) and a polar group containing a basic amine. Typically, CADs have a moderate to high log P-value and have a molecular weight below 1000 g/mol (e.g. ranging from 100 to 900, or from 200 to 800 g/mol) and can thus be considered as small molecules. In particular, the adjuvants of the present invention are cationic amphiphilic compounds having a log P value of at least 1, preferably at least 2, more preferably at least 3, or higher (up to 9, 10, or 11; such as e.g. a log P of between 3-9, between 3-10, between 3-11, between 4-9, between, 4-10 or between 4-11) and a maximum of (preferably exactly) one basic amine of which the conjugated acid has a pKa (also indicated as pKa1) of at least 5, 6, 7 or higher (up to 10, 11, 12 or 13). Such physicochemical properties can be calculated via dedicated software tools (e.g. ACD labs) and/or can be derived from (publically available) chemical compound databases, in particular DrugBank (Wishart D S, 2006).

The log P is a calculated log P value (c log P), based on a fragment approach for log P (octanol-water) prediction. Furthermore, the cationic amphiphilic compounds can comprise one or more basic amines. Of these basic amines no more than one basic amine, and in particular only one basic amine has a conjugated acid with a pKa of at least 5. More in particular, the cationic amphiphilic compounds can have a physiological charge (i.e. the molecular charge at physiological pH 7.4) of 0 or +1, and preferably a physiological charge of +1. The physiological charge can be calculated with dedicated software tools (e.g. cxcalc calculator function (formal charge at pH 7.4, Marvin 17.21.0, 2017, ChemAxon Ltd., Budapest, Hungary)).

In a particular embodiment, the adjuvant of the present invention is not chloroquine.

CADs tend to accumulate in the lysosomes due to their physicochemical properties and induce (phospho)lipidosis (PLD), which is characterized by the accumulation of (phospho)lipids in the lysosomal organelles of the affected cells. In this way, exposure of cells to CADs may induce an acquired lysosomal storage disorder (LSD) phenotype. It has been shown that the adjuvants of the present invention improve delivery of e.g. siRNA through the induction of a (phospo)lipidosis phenotype. The phenotype conversion was accompanied by a non-lethal lysosomal membrane permeabilization (LMP), which allowed the siRNA to diffuse towards the cytosol. Unexpectedly, this approach is not associated with high levels of cytotoxicity, which would be otherwise expected in case of significant lysosome disruption. Indeed, LMP is a hallmark of lysosomal cell death evoked by the release of lysosomal hydrolases, such as cathepsins, in the cell cytoplasm. LMP can be detected and quantified using a variety of assays as described in e.g. Aits et al., Methods Cell Biol., 2015. In particular, LMP can be visualized by the release of labeled dextrans (e.g. FITC-dextran) in the cytosol of the exposed cells. Non-lethal LMP refers to LMP that is not accompanied by a significant reduction of cell viability (i.e. non-lethal meaning <20% loss in cell viability compared to untreated control), as measured by a conventional cell viability assay (e.g. CellTiter-Glo® luminescent cell viability assay). Assays to determine the induction of (phospho)lipidosis comprise quantifying the (increased) lysosomal volume using lysosomotropic dyes (e.g. Lysotracker® Deep Red), intracellular quantification of lysosomal lipid accumulation (e.g LipidTOX™ assay) or visualization of intracellular lamellar bodies via transmission electron microscopy (TEM).

More specifically, the adjuvants of the present invention are functional inhibitors of the lysosomal acid sphingomyelinase (ASM). Structural inhibitors, which inhibit the activity of the enzyme acid sphingomyelinase via direct interaction with said enzyme, can also be envisioned. The adjuvants interfere with the binding of ASM to the membrane of intraluminal vesicles (ILVs) in late endosomes and lysosomes. Upon release in the lysosomal lumen, ASM is degraded by lysosomal proteolytic enzymes. ASM catalyzes the hydrolysis of sphingomyelin (SM) to ceramide and plays an important role in the maintenance of the lysosomal membrane integrity. In the present invention, it was demonstrated for the first time that such adjuvants can be used to improve cytosolic delivery of the lysosomally entrapped active agent in transfected cells by its inhibitory effect of ASM and subsequent (phospho)lipidosis and LMP induction.

As such, in one embodiment, the invention relates to a method for delivering an agent into the cytosol of a cell by in vitro, ex vivo or in vivo application whereby a nanocarrier coupled to or comprising an active agent is administered to a cell or subject prior, concurrent with or after the administration of an inhibitor of acid sphingomyelinase to said cell or subject. In one embodiment, the nanocarrier comprises the adjuvant as provided herein. The adjuvant may be encapsulated by the nanocarrier or it may be attached or coupled to a surface or surfaces thereof to form a conjugate.

The term 'inhibitor of ASM' relates to a compound (as such or as part of a nanocarrier or pharmaceutical composition comprising the nanocarrier) that upon its incubation with cells for 24 h at 37° C. in complete cell culture medium, induces a statistically significant inhibition (e.g. by using the methods as described herein) compared to untreated control of the activity of the enzyme acid sphingomyelinase (ASM) in said cells as determined via e.g. a whole cell lysate assay (as described e.g. in Kornhuber et al., 2008) or via colorimetric assays e.g. Amplex® Red assay.

As mentioned above, "functional inhibitors or FIASMAs" is a term that characterizes a large group of pharmacological compounds inhibiting the enzyme acid sphingomyelinase via an indirect, functional mechanism. Most known FIASMAs insert into the outer leaflet of the membrane of intraluminal vesicles (ILVs) in late endosomes and lysosomes and subsequently cause membrane-associated hydrolytic enzymes, such as ASM, to detach. Indeed, the cationic charge of FIASMAs in the lysosomal compartment interferes with the electrostatic attachment of the positively charged saposin domain of ASM to the negatively charged lipid bis(monoacylglycero)phosphate (BMP), which is highly abundant in lysosomes, in particular in ILVs. Upon detachment from the membrane, these enzymes are readily degraded within lysosomes. FIASMAs are structurally and pharmacologically diverse, but have common physico-chemical properties. FIASMAs are weak bases that typically comprise a lipophilic part, and are therefore denoted as "cationic amphiphilic drugs" (CADs), as described above. Hence in a specific embodiment of the present invention, the adjuvant is a cationic amphiphilic functional inhibitor of acid sphingomyelinase.

Exemplary adjuvant compounds of the present invention are shown in Table 1. In a particular embodiment the adjuvant of the invention is carvedilol, desloratadine, nortriptyline, salmeterol, terfenadine or indacaterol. The pKa values of the most basic amines (macroscopic pKa of the conjugated acid, pKa1) and the log P values of the compounds were predicted with J Chem for Office (version 17.21.0.1797, ChemAxon Ltd., Budapest, Hungary). The physiological charge (at pH 7.4) was calculated with the cxcalc calculator function (formal charge at pH 7.4, Marvin 17.21.0, 2017, ChemAxon Ltd., Budapest, Hungary). All compounds of the invention have a log P>3. As an example, terfenadine, salmeterol and nortriptyline contain only one basic amine and the conjugated acid of this amine has a pKa higher than 5. Carvedilol and desloratadine also contain a second amine (calculated via ACD/Labs (I-Lab 2.0—ilab.acdlabs.com) in the tricyclic part of their chemical structure, of which the conjugated acid has a pKa of −3.70±0.50 (carvedilol) and 3.99±0.20 (desloratadine), i.e. in both cases below 5.

TABLE 1

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (1) Thiothixene | 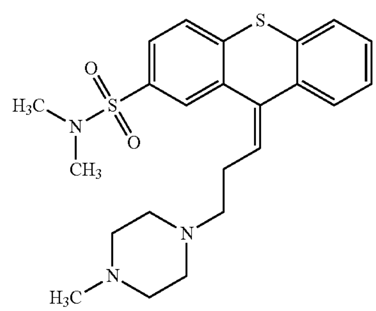 [SMILES: CN1CCN(CC/C=C2/c3ccccc3Sc3ccc(S(=O)(=O)N(C)C)cc32)CC1] | 443.62 | 3.36 | 8.16 | 1 | 0.11 |
| (2) Thioridazine hydrochloride | 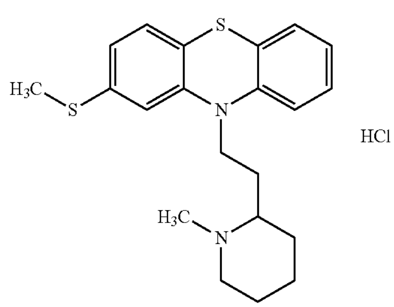 [SMILES: CSc1ccc2c(c1)N(CCC1CCCCN1C)c1ccccc1S2 ; Cl] | 407.03 | 5.47 | 8.93 | 1 | 0.13 |
| (3) Desloratadine | 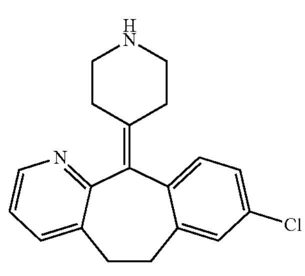 [SMILES: Clc1ccc2c(c1)CCc1cccnc1C2=C1CCNCC1] | 310.83 | 3.97 | 9.73 | 1 | 0.15 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (4) Tamoxifen | 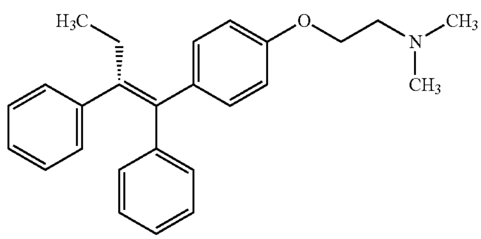 | 371.52 | 6.35 | 8.76 | 1 | 0.16 |
| (5) Perphenazine | 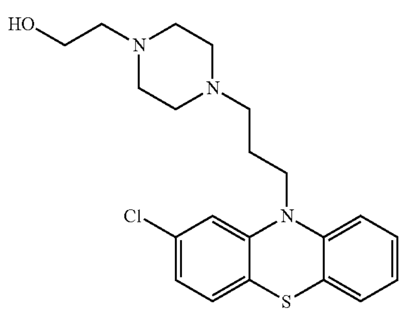 [SMILES: OCCN1CCN(CCCN2c3ccccc3Sc3ccc(Cl)cc32)CC1] | 403.97 | 3.69 | 7.81 | 1 | 0.16 |
| (6) Raloxifene hydrochloride | 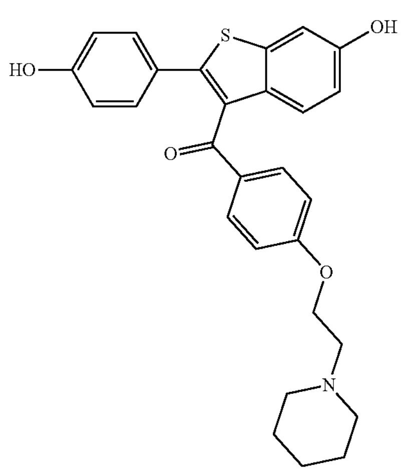 | 510.05 | 5.69 | 7.95 | 1 | 0.21 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (7) Loperamide hydrochloride | 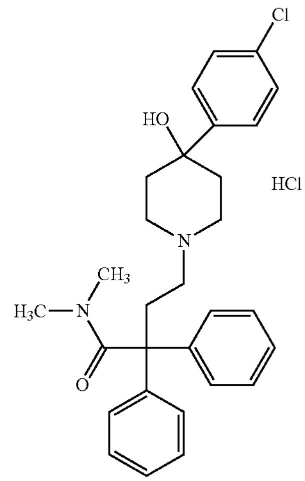 [SMILES: CN(C)C(=O)C(CCN1CCC(O)(c2ccc(Cl)cc2)CC1)(c1ccccc1)c1ccccc1 ; Cl] | 513.5 | 4.77 | 9.41 | 1 | 0.23 |
| (8) 5-Nonyloxytryptamine hydrochloride | 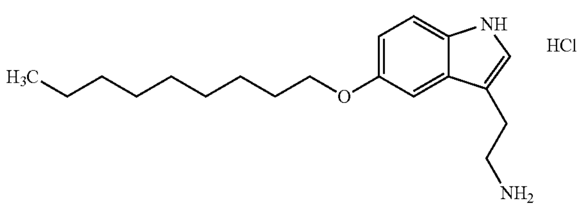 [SMILES: CCCCCCCCCOc1ccc2[nH]cc(CCN)c2c1 ; Cl] | 338.92 | 4.88 | 9.76 | 1 | 0.24 |
| (9) Paroxetine maleate | 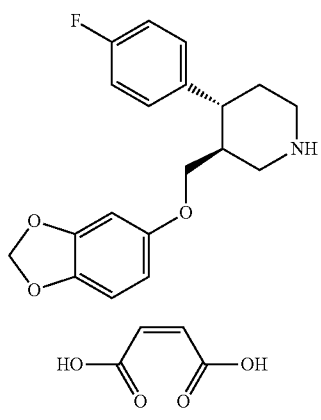 | 445.44 | 3.15 | 9.77 | 1 | 0.29 |
| (10) Clofazimine | 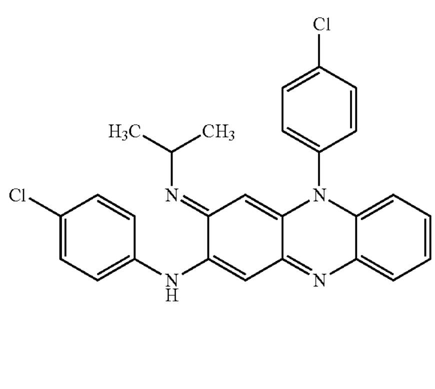 [SMILES: CC(C)/N=c1\cc2n(-c3ccc(Cl)cc3)c3ccccc3nc-2cc1Nc1ccc(Cl)cc1] | 473.4 | 7.30 | 6.63 | 0 | 0.35 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (11) Fluoxetine hydrochloride | 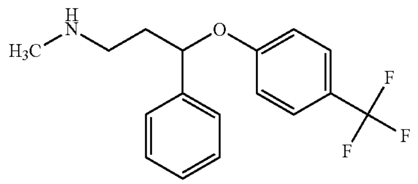 | 345.79 | 4.17 | 9.80 | 1 | 0.41 |
| (12) Toremifene citrate | | 598.09 | 6.27 | 8.76 | 1 | 0.45 |
| (13) Amiodarone hydrochloride | 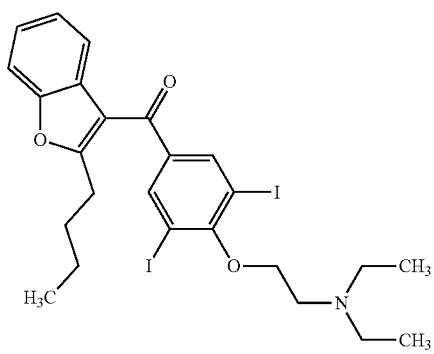 | 681.78 | 7.64 | 8.47 | 1 | 0.46 |
| (14) Saquinavir mesylate | 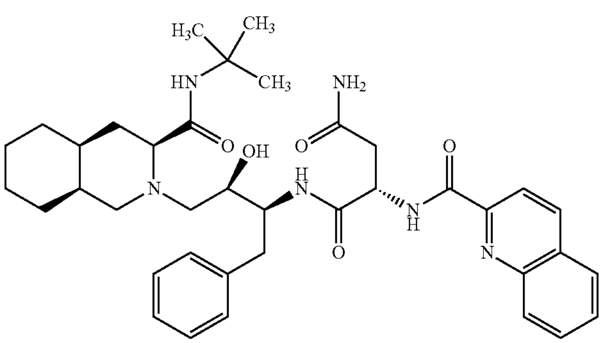 [SMILES: CC(C)(C)NC(=O)[C@@H]1C[C@@H]2CCCC[C@@H]2CN1C[C@@H](O)[C@H](Cc1ccccc1)NC(=O)[C@H](CC(N)=O)NC(=O)c1ccc2ccccc2n1] | 766.96 | 3.16 | 8.47 | 1 | 0.47 |

TABLE 1-continued

*Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).*

| Compound Number & Name | Structure | MW (g/mol) | LogP | pKa1 | Physiological charge (at pH 7.4) | Norm KD |
|---|---|---|---|---|---|---|
| (15) Indatraline hydrochloride | 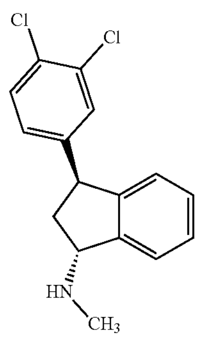 | 328.66 | 4.70 | 9.50 | 1 | 0.49 |
| (16) Duloxetine hydrochloride | 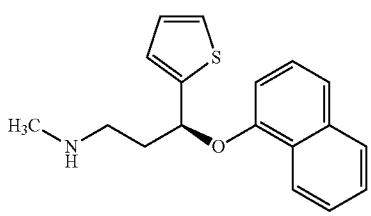 | 333.87 | 4.20 | 9.70 | 1 | 0.49 |
| (17) Clomipramine hydrochloride | 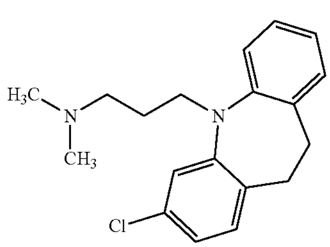 | 351.32 | 4.88 | 9.20 | 1 | 0.49 |
| (18) Salmeterol | 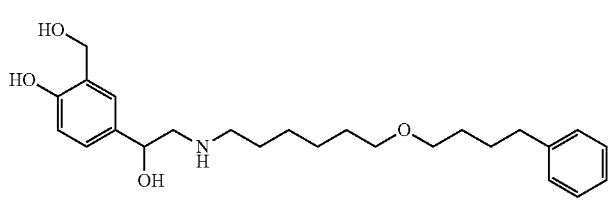 [SMILES: OCc1cc(C(O)CNCCCCCCOCCCCc2ccccc2)ccc1O] | 415.57 | 3.61 | 9.40 | 1 | 0.50 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (19) Mefloquine hydrochloride | 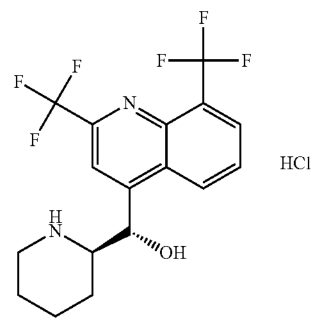 [SMILES: O[C@@H](c1cc(C(F)(F)F)nc2c(C(F)(F)F)cccc12)[C@H]1CCCCN1 ; Cl] | 414.78 | 4.11 | 9.46 | 1 | 0.52 |
| (20) Lofepramine | 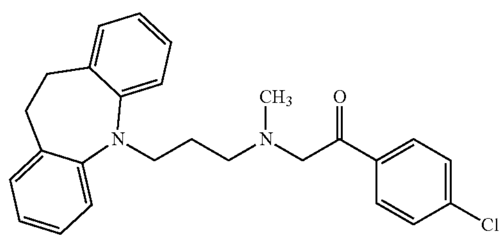 [SMILES: CN(CCCN1c2ccccc2CCc2ccccc21)CC(=O)c1ccc(Cl)cc1] | 418.97 | 6.11 | 6.53 | 0 | 0.55 |
| (21) Imatinib mesylate | 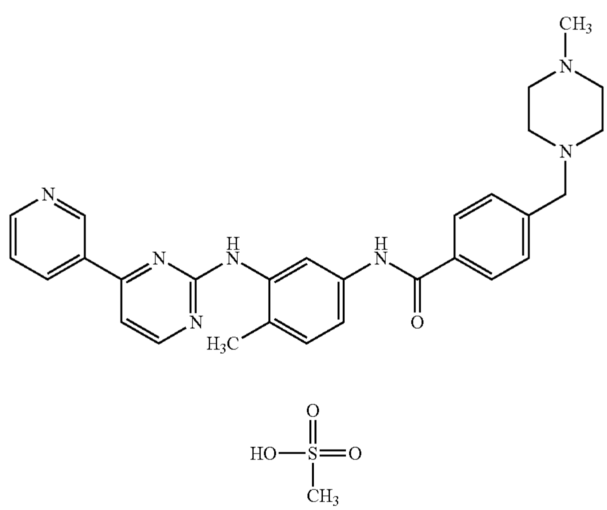 | 589.72 | 4.38 | 7.84 | 1 | 0.55 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (22) Nelfinavir mesylate | 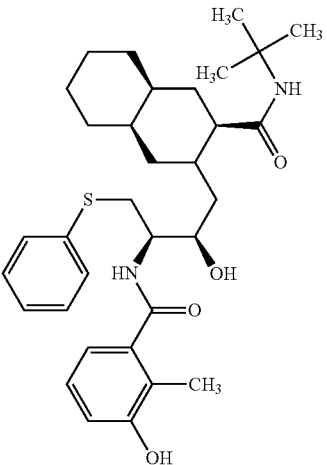 | 663.89 | 4.72 | 8.18 | 1 | 0.57 |
| (23) Miconazole nitrate | 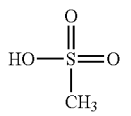 | 479.14 | 5.96 | 6.48 | 0 | 0.58 |
| (24) Trifluoperazine hydrochloride | 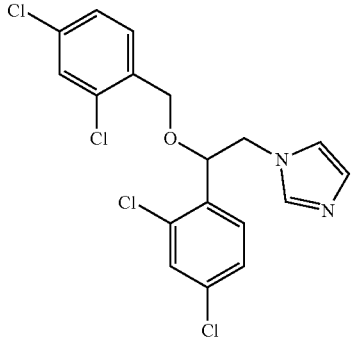 [SMILES: Clc1ccc(COC(Cn2ccnc2)c2ccc(Cl)cc2Cl)c(Cl)c1] | 443.96 | 4.66 | 7.99 | 1 | 0.60 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (25) Sertraline hydrochloride | 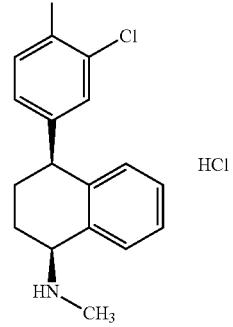 | 342.69 | 5.15 | 9.56 | 1 | 0.61 |
| (26) Carvedilol | 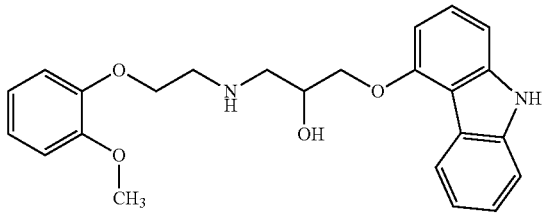 [SMILES: COc1ccccc1OCCNCC(O)COc1cccc2[nH]c3ccccc3c12] | 406.48 | 3.42 | 8.74 | 1 | 0.65 |
| (27) Aripiprazole | 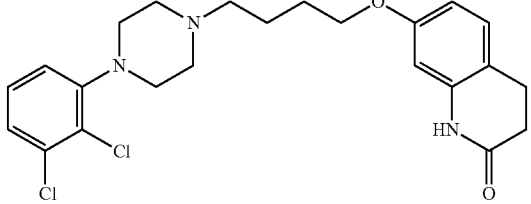 | 448.39 | 4.90 | 7.46 | 1 | 0.65 |
| (28) Azelastine hydrochloride | 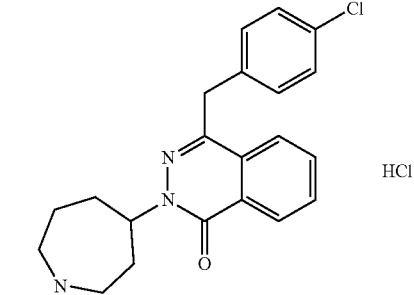 | 418.36 | 4.04 | 8.88 | 1 | 0.66 |
| (29) SB 205607 dihydrobromide | 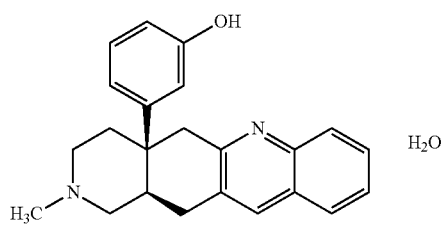 | 443.39 | 3.92 | 8.28 | 1 | 0.67 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (30) Econazole nitrate | 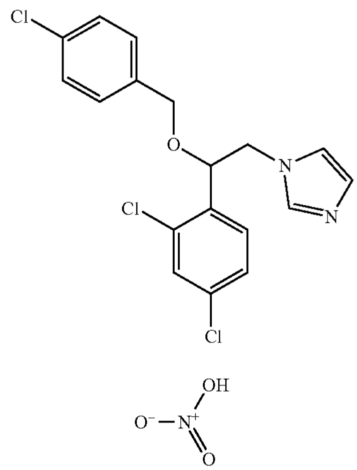 | 444.69 | 5.35 | 6.48 | 0 | 0.67 |
| (31) Amitriptyline hydrochloride | 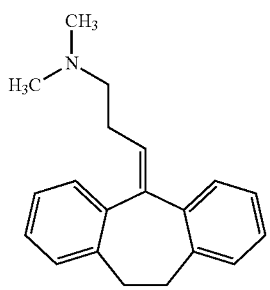 | 313.87 | 4.81 | 9.76 | 1 | 0.67 |
| (32) Cyproheptadine hydrochloride | 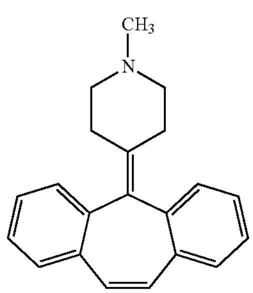 | 323.86 | 4.38 | 8.05 | 1 | 0.68 |
| (33) Benproperine phosphate | 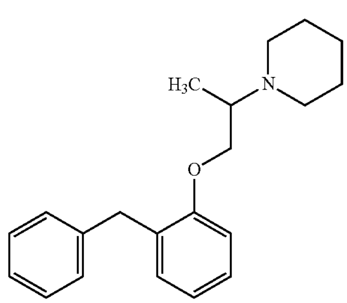 [SMILES: CC(COc1ccccc1Cc1ccccc1)N1CCCCC1] | 407.45 | 5.19 | 9.05 | 1 | 0.68 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (34) Dextromethorphan hydrobromide, monohydrate | 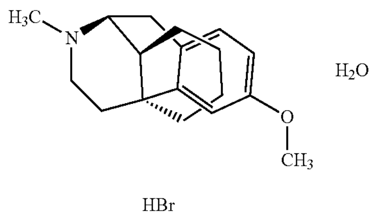 | 370.33 | 3.49 | 9.85 | 1 | 0.70 |
| (35) Rimcazole dihydrochloride | 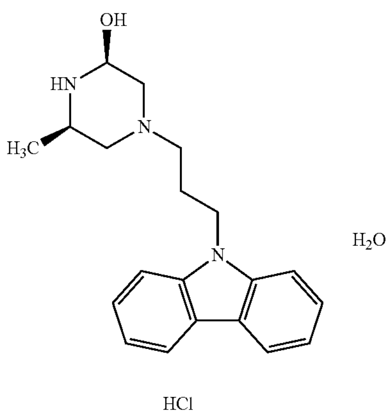 [SMILES: C[C@@H]1CN(CCCn2c3ccccc3c3ccccc32)C[C@H](O)N1 ; O ; Cl] | 375.94 | 3.69 | 9.81 | 1 | 0.71 |
| (36) Clomifene citrate | 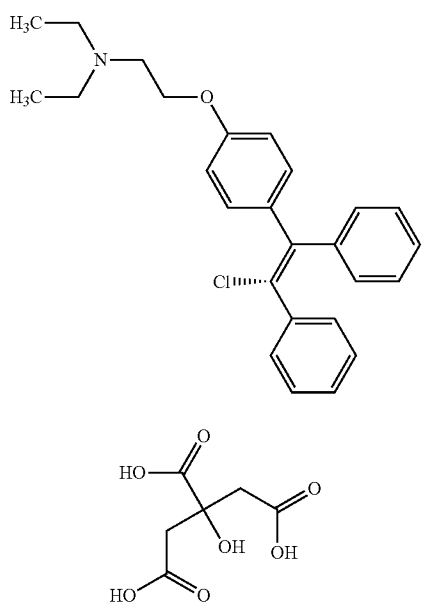 | 598.09 | 6.47 | 9.31 | 1 | 0.75 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (37) Imipramine hydrochloride | 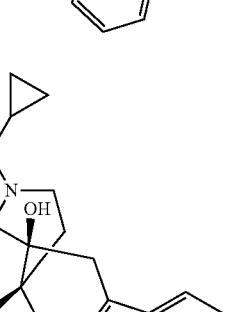 | 316.87 | 4.28 | 9.20 | 1 | 0.75 |
| (38) Naltrindole hydrochloride hydrate | 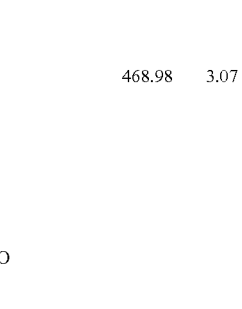 | 468.98 | 3.07 | 8.64 | 1 | 0.77 |
| (39) Prochlorperazine maleate | 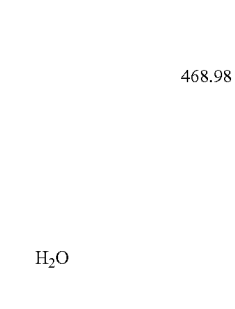 | 490.02 | 4.38 | 7.99 | 1 | 0.77 |
| (40) Chlorpromazine hydrochloride | 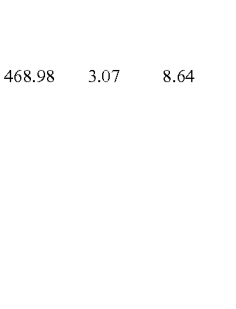 | 355.32 | 4.54 | 9.20 | 1 | 0.77 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (41) Haloperidol hydrochloride | 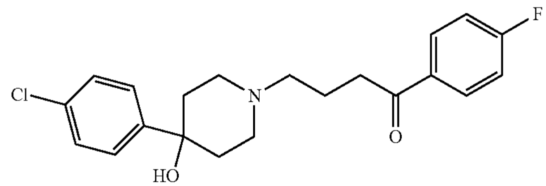 | 412.33 | 3.66 | 8.05 | 1 | 0.78 |
| (42) Hydroxyzine pamoate | | 762.28 | 3.41 | 7.45 | 1 | 0.78 |
| (43) Diphenoxylate hydrochloride | 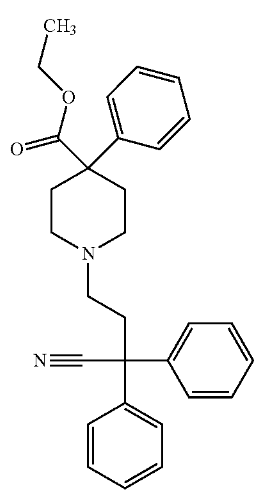 | 489.06 | 5.88 | 8.50 | 1 | 0.78 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (44) CGS 12066B dimaleate | 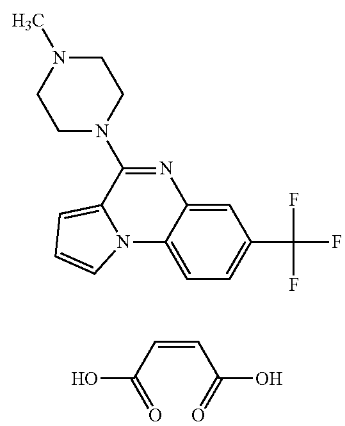 | 450.42 | 3.22 | 7.61 | 1 | 0.78 |
| (45) Amoxapine | 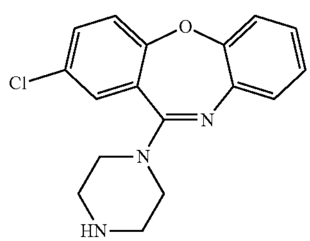 [SMILES: Clc1ccc2c(c1)C(N1CCNCC1)=Nc1ccccc1O2] | 313.79 | 3.08 | 8.83 | 1 | 0.78 |
| (46) Desipramine hydrochloride | 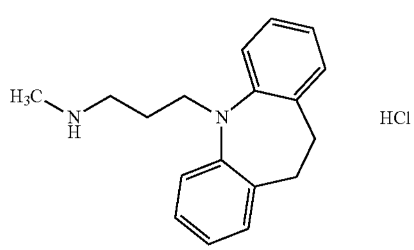 [SMILES: CNCCCN1c2ccccc2CCc2ccccc21 ; Cl] | 302.85 | 3.90 | 10.02 | 1 | 0.81 |
| (47) Olanzapine | 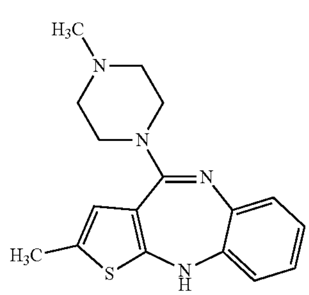 [SMILES: Cc1cc2c(s1)Nc1ccccc1N=C2N1CCN(C)CC1] | 312.44 | 3.39 | 7.24 | 1 | 0.83 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (48) Pizotyline maleate | 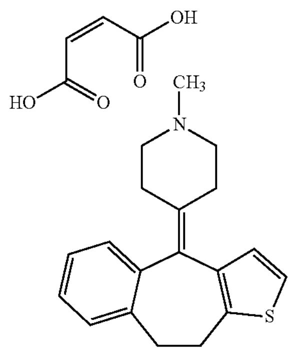 | 411.52 | 4.49 | 7.98 | 1 | 0.83 |
| (49) Naftopidil | 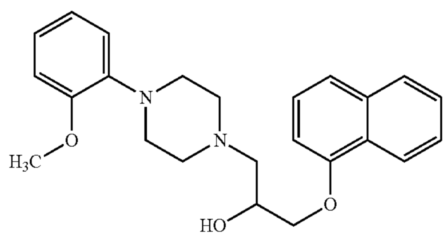 [SMILES: COc1ccccc1N1CCN(CC(O)COc2cccc3ccccc23)CC1] | 392.50 | 3.77 | 7.35 | 1 | 0.83 |
| (50) Verapamil hydrochloride | 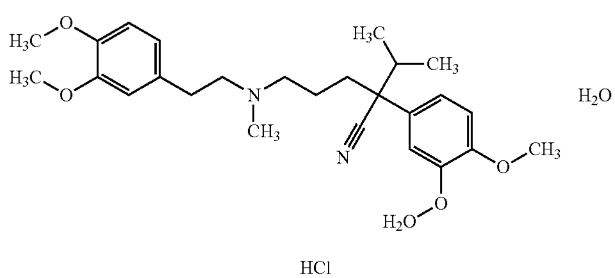 | 509.08 | 5.04 | 9.68 | 1 | 0.83 |
| (51) Clozapine | 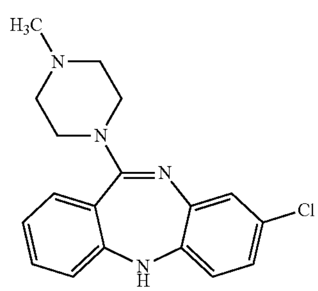 [SMILES: CN1CCN(C2=Nc3cc(Cl)ccc3Nc3ccccc32)CC1] | 326.83 | 3.40 | 7.35 | 1 | 0.85 |
| (52) Promethazine hydrochloride | 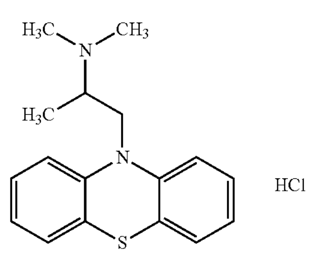 [SMILES: CC(CN1c2ccccc2Sc2ccccc21)N(C)C ; Cl] | 320.88 | 4.29 | 9.05 | 1 | 0.85 |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (53) SKF 83566 hydrobromide | 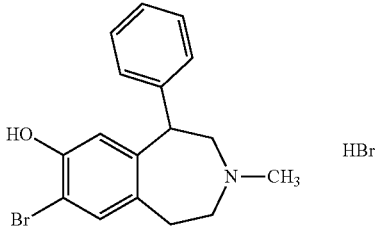 [SMILES: CN1CCc2cc(Br)c(O)cc2C(c2ccccc2)C1 ; Br] | 413.15 | 3.60 | 8.77 | 1 | 0.88 |
| (54) Ketoconazole | 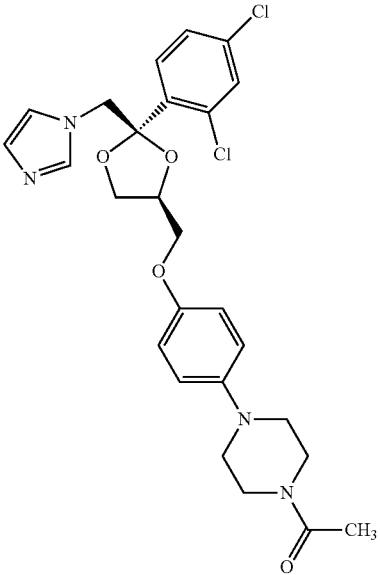 [SMILES: CC(=O)N1CCN(c2ccc(OC[C@H]3CO[C@](Cn4ccnc4)(c4ccc(Cl)cc4Cl)O3)cc2)CC1] | 531.43 | 4.19 | 6.42 | 0 | 0.89 |
| (55) Nortriptyline hydrochloride | 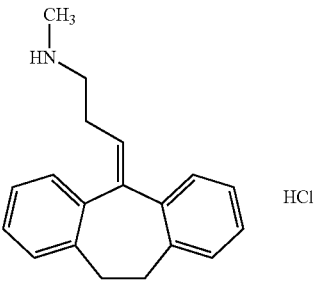 [SMILES: CNCCC=C1c2ccccc2CCc2ccccc21 ; Cl] | 299.84 | 4.43 | 10.47 | 1 | / |

TABLE 1-continued

Adjuvant compounds that comply with the CAD definition of the present invention (log P > 3, pKa1 > 5), and having a molecular weight (MW) of less than 1000 g/mol. (pKa1 = macroscopic pKa of the conjugated acid of the most basic amine, Norm KD = normalized knockdown v.s. siNG-DMSO control). Structures were obtained from JChem for Office (version 17.21.0.1797, ChemAxon Ltd., Budapest, Hungary).

| Compound Number & Name | Structure | MW (g/mol) | LogP | pKa1 | Physiological charge (at pH 7.4) | Norm KD |
|---|---|---|---|---|---|---|
| (56) Terfenadine | 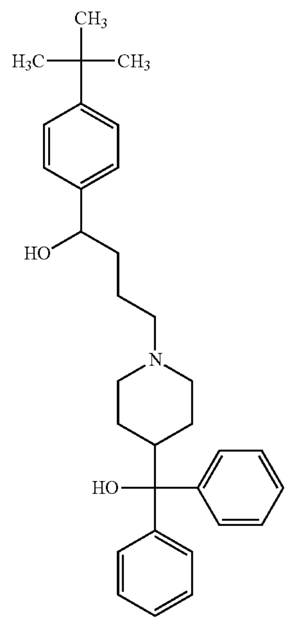 [SMILES: CC(C)(C)c1ccc(C(O)CCCN2CCC(C(O)(c3ccccc3)c3ccccc3)CC2)cc1] | 471.69 | 6.48 | 9.02 | 1 | / |
| (57) Indacaterol maleate | | 508.57 | 3.26 | 9.71 | 1 | / |

In a particular embodiment, the adjuvant compound of the present invention is selected from the compounds of table 1, more in particular from the list comprising carvedilol, desloratadine, nortriptyline, salmeterol, terfenadine or indacaterol.

It was furthermore demonstrated in the present invention that when a combination of adjuvants was applied in the methods or combination as provided herein, additive effects on gene silencing were observed. Hence, a combination of more than one, e.g. 2 or 3 or more, of the adjuvants as described herein can be used in the methods of the present invention.

The term "nanocarrier" as used herein can be interpreted broadly and refers to a carrier being used as a transport module for another substance, such as a drug, in particular a macromolecular drug, more in particular a nucleic acid. Such carriers can be particles between about 5 nm to about 10 µm in size. Nanocarriers are currently being studied for their use in drug delivery and range from sizes of diameter 5-1000 nm, in particular from about 5 to about 500 nm, more in particular from about 5 to about 300 nm. In particular, the size of the nanocarrier is such that it is capable of being taken up by a mammalian cell by endocytosis and is subsequently trafficked to endo-lysosomal organelles. Besides nanocarriers, also carriers with a size >1 µm can be internalized by phagocytic cell types (e.g. macrophages, dendritic cells) and are trafficked toward phago-lysosomes. Because of their small size, nanocarriers can deliver drugs to otherwise inaccessible sites around the body. Examples of carriers or nanocarriers include microspheres, core-shell microparticles, polyelectrolyte microparticles, metallic microparticles, metal-organic framework (MOF) materials, emulsions and microparticulate powders (e.g. obtained via spray drying), drug conjugates, polymer conjugates, polymeric nanoparticles, polymeric micelles, emulsions, lipid-based carriers, viral nanoparticles, extracellular vesicles, dendrimers, core-shell nanoparticles, carbon nanotubes, and metallic nanoparticles. Lipid-based carriers comprise solid lipid nanoparticles, liposomes and micelles. Examples of metallic nanoparticles are gold nanoshells and nanocages or iron oxide nanoparticles. The nanocarriers of the present invention may be formed from any suitable biocompatible materials, which may be biodegradable or non-biodegradable. Examples of suitable biodegradable materials include collagen, fibrin, chitosan, hyaluronic acid, dextran, poly (anhydrides), degradable polyesters, poly(hydroxy acids), poly(ortho esters), poly(propylfumerates), poly(caprolactones), polyamides, polyamino acids, polyacetals, biodegradable polycyanoacrylates, biodegradable polyurethanes, poly(glycerol sebacates), especially elastomeric poly(glycerol sebacates), and polysaccharides. Non-biodegradable, yet biocompatible, materials include polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, and poly(ethylene oxide). Those skilled in the art will recognize that this is not a comprehensive list of materials appropriate for the preparation of nanocarriers, but rather an illustrative list.

In a specific embodiment, the applied nanocarrier is capable of releasing the drug payload in the endosomes and/or endo-lysosomes, e.g. as a function of nanocarrier degradation or disassembly. In a specific embodiment, the applied nanocarrier is able to resist an acidic and degrading environment and hence is stable at low pH, e.g. a pH of less than about 5. The nanocarriers may be customized in terms of size, surface charge and attachment of any targeting moieties such as e.g. antibodies, peptides, folate, carbohydrates (such as mannose, galactose or GalNAc), haloperidol, anisamide, and cardiac glycosides or the like. Furthermore, the nanocarrier surface can be modified with poly(ethylene glycol) (PEG) or related polymers or moieties that are able to maintain nanocarrier colloidal stability, reduce nonspecific interactions and recognition by the immune system. Any type of nanocarriers may be used in the present invention, in particular, the nanocarriers are polymeric nanocarriers, more in particular cationic polymeric nanocarriers, and even more in particular dextran nanogels.

In a further embodiment, the nanocarriers of the invention preferably include a cationic agent embedded in the core or at or on the surface (also referred to as a cationic nanocarrier). Where the nanocarriers are to be used for complexation of nucleic acids as the therapeutic agent, the positively charged nanocarriers are believed to interact electrostatically with the negatively charged DNA/RNA molecules, which not only facilitates complexation of the therapeutic, but which may also protect the latter from enzymatic degradation. Preferably, the cationic agent may be a polycationic agent such as but not limited to chitosan, peptides (such as poly(L-lysine)), peptide derivatives (such as poly(L-lysine)-palmitic acid), polyethylenimine, poly(amido ethylenimine), and poly(amido amine)s. A preferred polycationic agent is a polymer, preferably a polysaccharide, more preferably dextran, which is functionalized with a reactive (meth)acrylate moiety and subsequently co-polymerized with a cationic (meth)acrylate monomer such as 2-aminoethyl methacrylate, 2-(diethylamino)ethyl methacrylate, 2-(dimethylamino)ethyl methacrylate, 2-N-morpholinoethyl methacrylate, 2-(tert-butylamino)ethyl methacrylate, 2-(diisopropylamino)ethyl methacrylate, [2-(methacryloyloxy)ethyl] trimethylammonium chloride.

In a specific embodiment, the nanocarrier is a cationic dextran nanogel, as described and prepared in De Backer et al., 2013 (incorporated herein by reference).

Hence, the nanocarriers are suitable for use with any (therapeutic) agent. The agent may be encapsulated by the nanocarrier or it may be attached to a surface or surfaces thereof to form a conjugate. In some cases, the encapsulation of the therapeutic agent is advantageous, as higher concentrations of a drug can be encapsulated than attached at the surface. Suitable methods for encapsulating agents inside nanocarriers are known to the skilled person and comprise electrostatic complexation, covalent coupling, hydrophobic interactions, passive loading, remote loading, salting-out, nanoprecipitation, emulsion-diffusion, solvent-evaporation, spray drying and emulsion polymerization. Typically such methods may be adapted depending upon the materials used to manufacture the nanocarriers and the chosen agent, which adaptation will be within the remit of the skilled person.

As used herein, the "active agent" may be a protein, peptide, lipid, chemical compound, genetic material (i.e. a nucleic acid) or any other (biologically) active molecule.

Examples of proteinaceous (therapeutic) agents that may be delivered intracellularly by the nanocarriers described herein include enzymes, peptides, antibodies and protein modulators. Alternatively, the agent may be a small molecule, such as e.g. daunorubicin, doxorubicin, vincristine, paclitaxel, docetaxel, amphotericin B, morphine, dexamethasone, retinoic acid and histamine, among others. Increasing the specificity of intracellular delivery of small molecules would not only reduce side effects but also the necessary amount of drug and, consequently, costs. The nanocarriers described herein may similarly increase the specificity of intracellular delivery of small molecules. This could be advantageous, particularly for anticancer drugs and such like, where minimizing the potential side effects and overcoming drug resistance is key. In a specific embodiment, the nanocarriers may also be used to release the small molecular adjuvants locally in the endosomes and/or endolysosomes, which could allow the efficient induction of LMP, using lower doses of the adjuvant.

In a particular embodiment, the active agent is genetic material, i.e. a nucleic acid, including but not limited to plasmid DNA, messenger RNA (mRNA), DNA antisense oligonucleotides, RNA antisense oligonucleotides (including e.g. triplex forming oligonucleotides, transcription factor decoy oligonucleotides, exon-skipping oligonucleotides and splice-correcting oligonucleotides), small non-coding RNAs (e.g. siRNA, dicer-substrate siRNAs (dsiRNA) or miRNA) and long non-coding RNAs. Particularly preferred are complexes of a nanocarrier and a small non-coding RNA or DNA/RNA antisense oligonucleotide (typically up to 30 nucleotides e.g. 13-25 nucleotides). RNA interference (RNAi) represents a powerful gene silencing mechanism wherein ~21 nt RNA duplexes, i.e. siRNAs, function as the effector molecules for sequence-specific mRNA cleavage, thereby inducing sequence-specific gene-silencing on the post-transcriptional level. Since synthetic siRNAs have been shown to activate the RNAi pathway and since they can be designed to target nearly any human gene, RNAi has become the method of choice to suppress gene expression for therapeutic purposes.

In a further embodiment, the nanocarriers include an imaging agent. As used herein, the term "imaging agent" can mean any agent that can be tracked non-invasively using magnetic resonance imaging (MRI), ultrasound, optical imaging (fluorescence, bioluminescence), confocal microscopy or such like. Suitable imaging agents include, for example fluorine compounds, such as perfluorocarbon (PFCs), and fluorescent labels, such as fluorescent dyes, well known to the skilled person. Examples of suitable fluorescent labels include fluorescein (such as fluoresceinamine or fluorescein isothiocyanate (FITC)), rhodamine, Alexa Fluor® dyes, DyLight® Fluor dyes, ATTO dyes, borondipyrromethene (BODIPY) dyes and such like.

The presence of an imaging agent permits the nanocarrier to be tracked in cells in vitro and/or in vivo. The imaging agent may be included in the nanocarrier by any suitable means including encapsulation, covalent conjugation, physical immobilisation (for example, by electrostatic attraction, hydrophobic interaction and such like), layer-by-layer (LBL) adsorption and so on. The particular method used will depend upon the particular imaging agent and the nanocarriers selected, and such methodology would be within the remit of a skilled person.

Furthermore, the nanocarrier described herein, and more specifically the coat or outer layer of the nanocarrier, may comprise a ligand or a cell trafficking agent, such as a nuclear localization signal, a mitochondrial localization signal, an ER signal peptide, an ER retrieval sequence or such like, as is described in the art.

The present invention thus relates to a combination of a nanocarrier comprising or coupled to an active agent and at least one adjuvant, in particular an inhibitor of the enzyme acid sphingomyelinase that induces lysosomal membrane permeabilization (LMP), for use as a medicament. The combination of the present invention is particularly useful for medical applications such as therapeutic, diagnostic or theranostic applications. Despite numerous efforts, endosomal escape remains an inefficient process up to date and consequently lysosomal entrapment is regarded as a non-functional dead end for nucleic acid based nanomedicines. In contrast, as current state-of-the-art endosomal escape strategies fail to deliver and lysosomal sequestration of nanocarriers seems inevitable, the method of the present invention targets the lysosomes for novel escape strategies. The method as described herein induces release of the accumulated active agent in the lysosomes by use of an adjuvant. Intracellular events can be more effectively affected and regulated upon intracellular delivery of different biologically active agents using said compositions. These active agents may modify or normalize the cellular function or may eliminate unwanted cells when needed. The changing of the cellular functionality may involve a change in a physico-chemical property of the cell, a change in proliferative property of the cell, a change in surviving ability of the cell, a change in secretory capacity of the cell, a change in migration property of the cell or a change in morphological phenotypical property of the cell. Hence, many clinical applications can be envisaged. For example, the adjuvant and the loaded nanocarriers or cells labeled with the nanocarriers, of the invention could be administered (concurrently or subsequently) to patients suffering from a disease or disorder whereby the development of the symptoms or conditions associated with said disease are prevented, delayed, alleviated, arrested or inhibited.

In a particular embodiment, the combination of adjuvants and nanocarriers are useful for the prophylaxis and/or treatment of various diseases such as cancer, disorders characterized by dysfunctional lysosomes, e.g. lysosomal storage diseases, diseases related to aging, neurodegenerative diseases, diseases with impaired SM/ceramide balance, and the like. Cancer cells are potentially more sensitive due to less stable lysosomes and lower ASM expression levels compared to their healthy counterparts.

In a further embodiment, therapies comprising a nanocarrier, an active agent and at least one adjuvant, and methods of treatment using such therapies are provided. In one embodiment, a therapy comprises a nanocarrier, an active agent and cationic amphiphilic compound as defined herein, the latter being in particular an ASM inhibitor, more in particular a FIASMA.

The invention further provides pharmaceutical compositions or delivery systems comprising the nanocarrier, the active agent and a pharmaceutically acceptable excipient, carrier and/or diluent, and optionally at least one adjuvant as described herein. The invention provides first and further medical uses of a combination of the nanocarrier (or the composition comprising it) and the adjuvant(s) as provided herein. More particular, the present invention provides a combination of a nanocarrier and at least one adjuvant for use in the intracellular delivery of an agent, especially a membrane-impermeable agent or a hydrophobic agent or drug.

A "pharmaceutically acceptable excipient" as referred to herein, is any known compound or combination of known compounds that are known to those skilled in the art to be useful in formulating pharmaceutical compositions. In one embodiment, the pharmaceutically acceptable excipient may be a solid. A solid pharmaceutically acceptable excipient may include one or more substances which may also act as stabilizers, flavouring agents, lubricants, solubilisers, suspending agents, fillers, glidants, compression aids, inert binders, sweeteners, preservatives, dyes, coatings, or tablet-disintegrating agents. The excipient may also be an encapsulating material. In powders, the excipient is a finely divided solid that is in admixture with the finely divided active agents according to the invention. Suitable solid excipients include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like. In addition, the pharmaceutical excipient may be a liquid, and the pharmaceutical composition may be in the form of a solution. Liquid excipients are used in preparing solutions, suspensions, emulsions, ionic liquids, syrups, elixirs and pressurized compositions. The nanocarrier, active agent and/or adjuvant according to the invention may be dissolved or suspended in a pharmaceutically acceptable liquid excipient such as water, an organic solvent, a mixture of both or pharmaceutically acceptable oils or fats. The liquid excipient can contain other suitable pharmaceutical additives such as stabilizers, solubilisers, emulsifiers, buffers, preservatives, sweeteners, flavouring agents, suspending agents, thickening agents, colours, viscosity regulators, stabilisers or osmo-regulators. Suitable examples of liquid excipients for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the excipient can also be an oily ester such as ethyl oleate and isopropyl myristate. Sterile liquid excipients are useful in sterile liquid form compositions for parenteral administration.

Liquid pharmaceutical compositions, which are sterile solutions or suspensions, can be utilised by, for example, subcutaneous, intrathecal, epidural, intraperitoneal, intravenous and intramuscular injection.

In a specific embodiment, the at least one adjuvant is used separately from the nanocarrier, and is administered prior to, next to, or after the administration of the nanocarrier/active agent. The invention thus encompasses a method for delivering an agent into the cytosol of a cell by in vitro, ex vivo or in vivo application whereby a nanocarrier comprising said agent is administered to a cell or subject prior to, concurrent with or subsequent to the administration of at least one adjuvant to said cell or subject. In one embodiment, the method comprises a step of administering a nanocarrier coupled to or comprising an active agent, and one or more steps of administering an adjuvant. More particular, the adjuvant is administered directly or shortly after the administration of the nanocarrier/active agent, in particular within a period of 72 hours or less, e.g. within about 48, 36, 24, 20, 15, 10, 8, 7, 6, 5, 4, 3, 2 or 1 hour(s).

In another embodiment, the adjuvant is associated with, covalently coupled to, or incorporated/encapsulated in the nanocarrier by methods well known to the person skilled in the art. As an example, the adjuvant can be incorporated in the aqueous core and/or the lipid membrane of lipid-based nanoparticles such as liposomes, the adjuvant can be part of a lipidic or polymeric micelle formulation, the adjuvant can be applied in polymeric nanoparticles such as polymer conjugates, polymer matrix nanoparticles and solid polymer nanoparticles and the adjuvant can be directly conjugated to the active agent, e.g. the siRNA.

The combination or compositions of the invention may be used in a monotherapy for treating, ameliorating, reducing the risk of or preventing a disease. Alternatively, the combination or compositions may be used as an adjunct to, or in combination with, known therapies which may be used for treating, ameliorating, reducing the risk of or preventing a disease.

Compositions comprising the nanocarriers may be administered in a number of ways, e.g. by oral administration, by inhalation (e.g. intranasally or orally), by injection (into the blood stream or directly into a site requiring treatment), as topical use, or incorporated within a slow- or delayed-release device. In a particular embodiment, the administration is by intramuscular, intravenous (bolus or infusion), subcutaneous (bolus or infusion), or intradermal (bolus or infusion) injection. In case the at least one adjuvant is used separately from the nanocarrier, the adjuvant can be administered in the same way as the nanocarrier/active agent. Alternatively, the adjuvant is administered via another route than the nanocarrier/active agent. Preferably, the adjuvant is administered orally or via any other route that allows self-medication.

The frequency of administration will be influenced by the half-life of the active agents within the subject being treated. Optimal dosages to be administered may be determined by those skilled in the art, and will vary with the particular adjuvants and nanocarriers or cells in use, the stability of the pharmaceutical composition, the mode of administration, and the advancement of the disease. Additional factors depending on the particular subject being treated will result in a need to adjust dosages, including subject age, weight, gender, diet and time of administration. The nanocarriers and adjuvants may be administered before, during or after onset of the disease, disorder or condition to be treated. Daily doses may be given as a single administration of the combination as described herein (e.g. a single daily injection). Alternatively, administration can be twice or more times during a day.

A "subject", as used herein, may be a vertebrate, mammal or domestic animal. Hence, medicaments, compositions or combinations according to the invention may be used to treat any mammal, for example livestock (e.g. a horse), pets, or may be used in other veterinary applications. Most preferably, the subject is a human being.

All of the features described herein (including any accompanying claims, abstract and drawings), and/or all of the steps of any method or process so disclosed, may be combined with any of the above aspects in any combination, except combinations where at least some of such features and/or steps are mutually exclusive.

EXAMPLES

Materials and Methods 1. siRNA Duplexes

The 21 nucleotide siRNA duplex against enhanced green fluorescent protein (eGFP; siEGFP) and the negative control siRNA duplex (siCTRL) were purchased from Eurogentec (Belgium). For cell uptake experiments, the siCTRL duplex was labeled with a Cy5 dye at the 5' end of the sense strand (Eurogentec, Belgium). Nuclease stabilized siEGFP and siCTRL duplexes (siSTABLE™) as well as the siGLO green transfection indicator were purchased from Dharmacon (USA). Finally, custom-designed siRNAs with the siSTABLE™ modification targeting polo-like kinase 1 (PLK1) was obtained from Dharmacon (USA). The sequences as well as modifications of the applied siRNA duplexes are summarized in Table 2.

TABLE 2 applied siRNA sequences and duplex modifications.

| siRNA | Modif. | Manufact. | Sense strand (5' → 3') | Antisense strand (5' → 3') |
|---|---|---|---|---|
| siCTRL[b] | / | Eurogentec | UGCGCUACGAUCGACGAUGtt (SEQ ID NO: 1) | CAUCGUCGAUCGUAGCGCAtt (SEQ ID NO: 2) |
| siCTRL[b] | Cy5-labeled[c] | Eurogentec | UGCGCUACGAUCGACGAUGtt (SEQ ID NO: 3) | CAUCGUCGAUCGUAGCGCAtt (SEQ ID NO: 4) |
| siCTRL[b] | Stabilized[d] | Dharmacon | UAGCGACUAAACACAUCAAUU (SEQ ID NO: 5) | UUGAUGUGUUUAGUCGCUAUU (SEQ ID NO: 6) |
| siEGFP[e] | / | Eurogentec | CAAGCUGACCCUGAAGUUCtt (SEQ ID NO: 7) | GAACUUCAGGGUCAGCUUGtt (SEQ ID NO: 8) |
| siEGFP[e] | Stabilized[d] | Dharmacon | CAAGCUGACCCUGAAGUUCUU (SEQ ID NO: 9) | GAACUUCAGGGUCAGCUUGUU (SEQ ID NO: 10) |
| siGLO | FAM-labeled[g] | Dharmacon | Not provided | Not provided |
| siPLK1[f] | Stabilized[d] 5'-P (antisense) | Dharmacon | CAACCAAAGUCGAAUAUGAUU (SEQ ID NO: 11) | UCAUAUUCGACUUUGGUUGUU (SEQ ID NO: 12) |

[a]Capital and lower case letters respectively represent ribonucleotides and 2'-deoxyribonucleotides;
[b]negative control duplex;
[c]the siCTRL duplex was labeled with a Cy5 dye at the 5' end of the sense strand;
[d]siSTABLE RNA strand modification by Dharmacon for use in nuclease-rich environments;
[e]siRNA duplex targeting enhanced green fluorescent protein;
[f]siRNA duplex against polo-like kinase 1;
[g]Fluorescent siCTRL duplex modified to translocate to the nucleus upon successful transfection.

2. NG Complexation

The cationic dextran nanogels (NGs) were prepared via an inverse mini-emulsion photopolymerization method, as described previously (De Backer, 2013). A 2 mg/mL dispersion of lyophilized NG (dex-HEMA with a degree of substitution (DS) of 5.2) was prepared in ice-cooled nuclease free water and sonicated briefly (amplitude 10%). Subsequently, equal volumes of appropriate NG and siRNA dilutions in N-2-hydroxyethylpiperazine-N'-2-ethanesulfonic acid (HEPES) buffer (pH 7.4, 20 mM) were mixed to a final volume of 100 µL and were allowed to complex for 15 minutes at room temperature. The same volume of HEPES buffer was added to this dispersion, followed by Opti-MEM® (Invitrogen, Belgium) to a final volume of 1 mL. This complexation procedure was applied for all cell-based experiments and resulted in a 30 µg/mL NG dispersion loaded with 2 nM siRNA (0.067 pmol siRNA/µg NGs), unless indicated otherwise. In case of the National Institutes of Health Clinical Collection (NIHCC) screen experiments, equal volumes of appropriate NG and siRNA dilutions in HEPES buffer (pH 7.4, 20 mM) were mixed to a final volume of 800 µL and were allowed to complex for 10 minutes on ice. Next, Opti-MEM® was added to a final volume of 4 mL, resulting in a 30 µg/mL NG dispersion loaded with 1 nM siRNA (0.033 pmol siRNA/µg NGs).

3. Preparation of RNAiMAX Lipoplexes, Transfection and Adjuvant Treatment

Lipofectamine® RNAiMAX (Invitrogen, Belgium) was applied as prescribed by the manufacturer. In short, equal volumes of RNAiMAX and siRNA dilutions were mixed and allowed to complex during 5 minutes at room temperature. Transfection occurred in Opti-MEM®. According to the guidelines, 5 pmol siRNA/well was applied to obtain optimal transfection efficiencies. To allow comparison with the siNG transfection methods, the RNAiMAX lipoplexes were additionally further diluted to 0.6 pmol siRNA/well. In case of adjuvant treatment after RNAiMAX transfection, a concentration of 40 µM desloratadine (DL) was applied for 2 hours, using the same protocol as the siNG transfection. Of note, a single biological replicate was performed with three technical replicates and data are represented as the mean±SEM.

4. Preparation of DOTAP-DOPE Liposomes, Transfection and Adjuvant Treatment

DOTAP (2,3-dioleoyloxy-propyl)-trimethylammonium)—DOPE (1,2-dioleoyl-sn-glycero-3-phosphoethanolamine) liposomes (LPS) were prepared via the lipid film hydration method. All lipids were obtained from Avanti Polar Lipids, Inc. (Alabaster, Ala., USA) as solutions in chloroform. Appropriate volumes of the lipid solutions were mixed in a round bottom flask to obtain a 1:1 molar ratio. Through rotary evaporation under vacuum at 40° C., a lipid film was created and subsequently hydrated using 1 mL HEPES buffer (pH 7.4, 20 mM). The obtained mixture was vortexed and sonicated 1 minute at 10% amplitude to obtain a monodisperse 2 mM LPS dispersion (total lipid concentration). Subsequently, the DOTAP-DOPE LPS were complexed with siRNA at a charge ratio equal to 8. Hereto, appropriate dilutions of the LPS in HEPES buffer were added to an appropriate siRNA dilution. This mixture was allowed to complex at room temperature for 30 minutes prior to further dilution in Opti-MEM® and transfection. The applied siRNA concentrations per well were 0.25, 0.5 and 1 nM. In case of compound adjuvant treatment before/after DOTAP-DOPE LPS transfection, a concentration of 40 µM desloratadine (DL) was applied for 2 hours (just before, immediately after or 20 hours after transfection). Of note, a single biological replicate was performed for each experiment with three technical replicates and data are represented as the mean±SEM.

5. Cell Lines and Cell Culture Conditions

All experiments were performed on the alveolar epithelial carcinoma cell line H1299 of which both the wild type (H1299_WT) and the eGFP-expressing variant (H1299_eGFP) were applied. Complete cell medium was prepared by supplementing RPMI 1640 culture medium with 10% fetal bovine serum (FBS, Hyclone™, Thermo Fisher Scientific, Belgium), 2 mM L-Glutamine and 100 U/mL penicillin/streptomycin. The cell lines were cultured in a humidified atmosphere containing 5% $CO_2$ at 37° C. and culture medium was renewed every other day unless the 80% confluence level was reached. In this case, the cells were split using 0.25% trypsin-EDTA. All products were purchased from Invitrogen (Belgium) unless specifically mentioned otherwise.

6. siNG Transfection and Sequential Adjuvant Treatment

Cells were transfected with siNGs (0.6 pmol siRNA/well) during 4 hours at 37° C. in a humidified atmosphere containing 5% $CO_2$. Subsequently, the NG dispersion was removed, the cells were washed once with phosphate buffered saline (PBS, Invitrogen, Belgium) and received 0.5 mL fresh cell medium. In case of CAD treatment, 0.5 mL cell medium containing 10, 20 or 40 μM nortriptyline (NT, Sigma-Aldrich), salmeterol (ST, Sigma-Aldrich), carvedilol (CD, Sigma-Aldrich) or desloratadine (DL, Sigma-Aldrich) was applied. For testing different compounds (β2 agonists) from a stock solution in DMSO (25 mM), salmeterol xinafoate (Sigma-Aldrich; 604 g/mol), salbutamol hemisulfate (Sigma-Aldrich; 229 g/mol), indacaterol maleate (TCI Europe; 509 g/mol) and formoterol fumarate hemisulfate (Sigma-Aldrich; 421 g/mol) dilutions of 10 μM, 20 μM and 40 μM were made in cell culture medium. Additionally, 5 μM NT and DL were tested alone as well as in the following combinations: 5 μM+5 μM, 10 μM+10 μM and 20 μM+20 μM. Furthermore, dextromethorphan (DX) was tested in the following concentration range: 10, 20, 40, 80, 120, 160 and 200 μM. Terfenadine (TF) was tested in the concentration range: 1, 2, 3, 4 and 5 μM. In additional control experiments we applied cell medium containing 10, 20 or 40 μM chloroquine (CLQ), 30 μM U18666A or 300 μM 2-hydroxy oleic acid (2-OHOA), the latter either alone or in combination with 10 μM DL. Compound stock solutions were prepared in sterile-filtered BioPerformance Certified dimethyl sulfoxide (DMSO, Sigma-Aldrich, Belgium). The final DMSO concentration brought onto the cells did not exceed 0.16%. All adjuvant treatments were performed in cell medium and lasted 20 hours, unless specifically mentioned otherwise. Afterwards, the small molecule containing cell medium was removed and cells were kept in 1 mL fresh cell medium for an additional 24 hours until analysis. In a final set of experiments regarding the controlled siRNA release from the lysosomal compartment, the DL incubation time was reduced to 2 hours without further changes to the protocol timeline. This treatment time was also applied in the experiment where cells were exposed daily or every other day to DL over a period of 9 days.

7. Quantification of NG Uptake with Flow Cytometry

The H1299_eGFP cells were seeded similar to the silencing experiments described herein. Here, NGs were loaded with a mixture of 90% siCTRL and 10% Cy5-labeled siRNA to enable detection via flow cytometry. Further sample preparation occurred as described herein. Following 4 hours of incubation, the cells were washed with PBS containing 0.1 mg/mL dextran sulphate sodium salt (Sigma-Aldrich, Belgium) to remove surface bound complexes. This way, only the NGs that were actually internalized will be detected. Subsequently, sample preparations for flow cytometry were performed. The samples were analyzed with the FACSCalibur™ flow cytometer, collecting 15000 events per sample. The Cy5-labeled siRNA was excited using the red laser line and the fluorescence was detected with the 661 nm±16 nm filter. Finally, data analysis was performed using the FlowJo software (Tree Star Inc.).

8. Measuring the siNG Transfection Efficiency

For silencing experiments, H1299_eGFP cells were seeded in 24 well plates at a density of 35000 cells/well and were allowed to settle overnight. Subsequently, the cells were transfected and treated with small molecular adjuvants as described previously. Note that for every siEGFP or siPLK1 condition an siCTRL sample was included to account for potential off target effects. SiNG-mediated eGFP silencing was determined by flow cytometry. Sample preparation consisted of washing the cells with PBS followed by detachment with 0.25% trypsin-EDTA. The cells were collected, centrifuged during 5 minutes at 300 g, resuspended in 300 μL flow buffer and kept on ice until analysis. For each sample the forward and side scatter as well as the green fluorescent signal were measured for at least 5000 cells. The samples were excited with the 488 nm laser line and the signal was detected with the 530/30 filter using the FACSCalibur™ flow cytometer (BD Biosciences, Belgium) and BD CellQuest™ acquisition software. Finally, data analysis was performed using the FlowJo software (Tree Star Inc.) and the calculated % eGFP expression is presented as the mean±standard error of the mean (SEM).

When assessing the kinetics of the eGFP signal over an extended period of time, the eGFP signal was measured daily. Hereto, treated cells were passaged every other day and reseeded in new 24 well plates during sample preparation for the flow cytometry measurements. A similar strategy was applied in the experiment where cells were exposed daily or every other day to DL over a period of 9 days.

The silencing potential of siPLK1-NGs was established through evaluating the cell viability. Hereto, we applied the CellTiter GLO® assay (Promega, Belgium) according to the manufacturer's guidelines. Before initiating the assay, the culture plates and reconstituted assay buffer were placed at room temperature for 30 minutes. Next, the culture medium was replaced by 250 μL fresh cell medium and an equal volume of assay buffer was added. To induce complete cell lysis, the plates were shaken during 2 minutes and the signal was allowed to stabilize the following 10 minutes. 100 μL from each well was subsequently transferred to an opaque 96-well plate, which was measured with a GloMax® 96 Microplate Luminometer (Promega, Belgium). Three biological replicates were performed and data are expressed as the mean cell viability±SEM.

9. Cell Viability Following CAD Incubation

The H1299_eGFP cells were seeded, transfected and treated with the CADs similar to the silencing experiments. Please note that we only applied siCTRL-loaded NGs in this set of experiments. With the interest of evaluating the possible effect of our treatment on cell viability, the CellTiter GLO® assay was performed as described above. Again, three biological replicates were performed and data are expressed as the mean±SEM.

10. Screening the National Institutes of Health Clinical Collection (NIHCC) for Identification of Additional siRNA Delivery Adjuvants a. Compound Library Stock Preparation The NIHCC library was acquired from Evotec (San Francisco, Calif., USA), which supplied the DMSO-dissolved compounds at a concentration of 10 mM. Stock plates were made by transferring 2 μL of each compound to a new 96 well plate, followed by dilution to 10 µL with sterile-filtered BioPerformance Certified dimethyl sulfoxide (DMSO, Sigma-Aldrich, Belgium), resulting in a concentration of 2 mM for each compound. Two µL of the latter stock solutions were diluted with 198 µL serum-containing complete cell medium directly before use to give a final concentration of 20 µM for each drug. The final DMSO concentration brought onto the cells (both compound-treated and DMSO control) was 1%.

b. Screening Protocol

The adjuvant effect of 700 small molecules, included in the National Institutes of Health Clinical Collection (NIHCC), on the siNG-mediated eGFP silencing was determined by flow cytometry. H1299_eGFP cells were seeded in 96 well plates at a density of 7500 cells/well (100 µL/well) and were allowed to settle overnight. The edge wells were filled with 100 µL complete cell culture medium to reduce evaporation in the cell-containing wells. Next, the cells were transfected with siNGs (0.1 pmol siRNA/well, prepared as described previously) during 4 hours at 37° C. in a humidified atmosphere containing 5% $CO_2$. Subsequently, the NG dispersion was removed and the cells received 50 µL fresh (DMSO control) or compound-containing complete cell culture medium (20 µM). Each 96 well plate contained a siNG-DMSO control (n=4, 4 siCTRL and 4 siEGFP conditions) and 50 wells treated with 25 compounds (20 µM, n=1, 1 siCTRL and 1 siEGFP condition). After 20 hours, the small molecule containing cell medium (and DMSO control) was removed and cells were kept in 50 µL fresh cell medium for an additional 24 hours until flow cytometry analysis. Sample preparation consisted of detachment with 30 µL 0.25% trypsin-EDTA, neutralization with 120 µL cell medium and a transfer of the cell suspensions to a U-bottom 96 well plate, which was centrifuged during 5 minutes at 500 g. After removal of 120 µL supernatant, the cells were resuspended in 80 µL flow buffer (PBS with 1% FBS and 0.1% sodium azide) and kept on ice until analysis. For each sample the forward and side scatter as well as the green fluorescent signal of single cells were measured for 100 seconds at a flow rate of 25 µL/min. The samples were excited with the 488 nm laser line and the signal was detected with the 530/30 filter using the Attune™ NxT flow cytometer with the Attune™ auto sampler (Applied Biosystems™ by Life Technologies™, Foster City, Calif., USA) and Attune™ NxT acquisition software. Finally, data analysis was performed using the FlowJo software (Tree Star Inc.) and data were exported into Microsoft® Excel® ($16^{th}$ version, Microsoft Corp., Redmond, Wash., USA) for hit classification.

c. Data Analysis and Identification of Hits

Within each 96 well plate, a % eGFP expression was calculated for all the compound-treated (n=1) and DMSO control-treated (n=4) cells. For every plate, hits were defined as compounds that caused a decrease in % eGFP expression of more than 3 times the standard deviation (SD) on the % eGFP expression obtained with the DMSO control (values outside the 99.7% confidence interval (CI) of the DMSO control siNG-treated cells). The pKa values of the most basic amines (macroscopic pKa of the conjugated acid, pKa1) and the log P values of the compounds were predicted with J Chem for Office (version 17.21.0.1797, ChemAxon Ltd., Budapest, Hungary). The physiological charge (at pH 7.4) was calculated with the cxcalc calculator function (formal charge at pH 7.4, Marvin 17.21.0, 2017, ChemAxon Ltd., Budapest, Hungary). CADs were defined as described previously (log P>3 and pKa1>5).

11. Release of FITC-Dextrans and Oligonucleotides into the Cytosol

H1299_WT cells were seeded at 105000 cells/dish in 35 mm diameter glass bottom microscopy dishes (Greiner Bio-One GmbH, Germany) and were allowed to settle overnight. To visualize the FITC-dextran release, a 1 mg/mL dispersion of 10 kDa FITC-dextrans (Sigma-Aldrich, Belgium) in complete cell medium was added during 1 hour at 37° C. in a humidified atmosphere containing 5% $CO_2$. To assess oligonucleotide escape, the NGs were first loaded with 100 nM Alexa Fluor 647-labeled oligonucleotides (21-mer) (Eurogentec, Belgium) according to the procedure described for siRNA complexation. Of note, these oligonucleotides transfer to the nucleus upon release into the cytosol (Rehman et al., ACS Nano, 2013). Following four hours of NG transfection or 1 h incubation with FITC-dextrans, the cells were washed with PBS and received 1.5 mL fresh cell medium with or without 10, 20 or 40 µM DL. After an additional incubation period of 20 hours, the cell medium was removed and nuclei were labeled with Hoechst (Molecular Probes™, Belgium) in cell medium during 15 minutes at 37° C. Finally, the Hoechst solution was removed, fresh cell medium was added and cells were kept at 37° C. in a humidified atmosphere containing 5% $CO_2$ until imaging.

The samples were imaged using a laser scanning confocal microscope (LSCM, C1si, Nikon) and a 60× oil immersion Plan Apo objective (Nikon, Belgium). The 408, 488 and 633 nm laser lines were applied to respectively excite the Hoechst labeled nuclei, the FITC-dextrans and oligonucleotides. During data analysis with the ImageJ image processing software (NIH) both the total cell number and amount of cells with a diffuse FITC-dextran labeling or oligonucleotide-positive nuclei were counted. Data are represented as the % of cells with a diffuse FITC-dextran signal for minimum 225 cells per condition in 10 images and the % of cells with oligonucleotide-positive nuclei for at least 180 cells in 10 images.

12. Quantification of Lysosomal Volume Using Flow Cytometry

H1299_eGFP cells were seeded, transfected and treated with the CADs as described previously for the cell viability experiments. Following 20 hours of CAD treatment, the lysosomes were labeled with the LysoTracker® Deep Red (LDR) probe (Molecular Probes™, Belgium) through incubation with 1 mL of 75 nM LDR in cell medium for 30 minutes at 37° C. Further sample preparations were carried out as previously described for the silencing experiments. Using the FACSCalibur™ flow cytometer and BD CellQuest™ acquisition software, the LDR signal was detected with the 661/16 filter following excitation with the 633 nm laser line for at least 15000 cells per sample. Experiments were performed in biological triplicate and fold changes in LDR signal intensity are expressed as the mean±SEM.

13. Visualizing Lysosomes with Confocal Microscopy

H1299_WT cells were seeded as specified for the FITC-dextran release experiment and transfected with siNGs followed by a 20 hour DL treatment. After removal of the DL-containing cell medium, cells were washed with PBS and incubated with 75 nM LysoTracker® Red DND-99 (Molecular Probes™, Belgium) in cell medium during 30 minutes at 37° C. Next, the dye was removed, cells were washed with PBS and fixed with 4% paraformaldehyde (PFA) during 15 minutes at room temperature. Finally, the cells were washed twice with PBS, covered with Vectashield antifade mounting medium containing DAPI (Vector Laboratories, USA) and stored at 4° C. until imaging. A LSCM and 100× oil immersion Plan Apo objective (Nikon, Belgium) objective were applied for imaging. The 408 nm and 561 nm laser lines respectively excited the DAPI labeled nuclei and LysoTracker® Red DND-99 stained lysosomes. The LysoTracker® Red DND-99 signal intensity and area were determined using the ImageJ software in at least 115 cells from minimum 11 images.

14. Phospholipidosis Detection with LipidTOX™ Red

H1299_WT cells were seeded and allowed to settle overnight as detailed previously. Next, the cells were incubated with a mixture of a 1/1000 dilution of the LipidTOX™ red phospholipidosis detection reagent (Thermo Fisher Scientific, USA) and the desired CAD in complete cell medium. Upon 20 hour incubation, the cells were fixed with 4% PFA and stored at 4° C. covered in Vectashield antifade mounting medium containing DAPI. Imaging occurred with a LSCM and a 100× oil immersion objective. DAPI and the LipidTOX™ red phospholipidosis dye were respectively excited with the 408 nm and 561 nm laser lines and the signal intensity was determined with Image J in minimum 30 cells from 5 images per condition.

15. Cholesterol Detection with Filipin

Following H1299_WT cell seeding, transfection and DL treatment, the cells were washed once with PBS and fixed with 4% PFA during 1 hour. After washing the samples with PBS, the remaining PFA was quenched with a 1.5 mg/mL glycine solution in PBS during 10 minutes. Next, a 0.1 mg/mL filipin solution in PBS containing 10% FBS was applied for 2 hours. Afterwards, the cells were washed once with PBS containing FBS, once with PBS and finally stored at 4° C. in Vectashield without DAPI (Vector Laboratories, USA). All steps of this labeling procedure were executed at room temperature. The samples were imaged with a LSCM and a 100× oil immersion objective following excitation with the 408 nm laser line.

16. Sphingomyelin Detection with Lysenin

Cell seeding, transfection and DL treatment of the H1299_WT cells occurred similar to the previous microscopy experiments. The subsequent staining procedure was carried out at room temperature. Following one washing step with PBS, the cells were fixed with 4% PFA during 15 minutes. The fixative was removed, the cells washed twice with PBS and permeabilized with 0.5% Tween 20 for 15 minutes. Next, the cells were washed twice with blocking buffer (BB, 2 wt % bovine serum albumin (Amresco, USA) in PBS) and kept in BB during 30 minutes. Upon removal, the cells were incubated 2 hours with a 1 µg/mL lysenin (Sigma-Aldrich, Belgium) solution in BB. Next the cells were washed twice with PBS before incubating 1 hour with the lysenin rabbit anti-human antiserum (1:500 in BB, Peptanova, Germany). Before and after the subsequent 1 hour incubation period with the secondary goat anti-rabbit Alexa Fluor 647 antibody (1:500 in BB, Molecular Probes™, Belgium), cells were washed with BB. Finally the cells were washed with PBS and stored at 4° C. covered with Vectashield containing DAPI. Using the 408 nm and 633 nm laser lines, the nuclei and sphingomyelin were excited respectively and detected with a LSCM and a 60× oil immersion objective.

17. siGLO Green Transfection Indicator

H1299_WT cells were seeded as described previously. For this experiment, NGs were complexed with 100 nM green fluorescent siRNA (siGLO, Dharmacon, USA) prior to transfection. Following transfection and 40 µM DL treatment, the cells were fixed with 4% PFA and stored in Vectashield containing DAPI as previously mentioned. The samples were imaged with a LSCM and a 100× oil immersion objective following excitation with the 408 nm and 488 nm laser line to visualize the DAPI and siGLO signal respectively.

18. Statistical Analysis

Results are represented as the mean±SEM unless indicated otherwise. Statistical analysis was performed using the 6th version of the GraphPad Prism software. One-way ANOVA combined with the post-hoc Dunnett test or the Bonferroni multiple comparison test was applied to compare multiple conditions whereas the student t-test was used for direct comparison of 2 conditions.

Results

1. CAD Treatment Enhances siRNA-Mediated Gene Silencing

First we evaluated if the adjuvant treatment with nortriptyline (NT), salmeterol (ST), carvedilol (CD) or desloratadine (DL) enhanced the gene silencing potential of siRNA-loaded dextran nanogels (siNGs) in a non-small cell lung cancer cell line (H1299) that stably expresses the enhanced green fluorescent protein (eGFP). The NGs were loaded with a suboptimal siRNA concentration, namely 2 nM (corresponding to 0.067 pmol siRNA/µg NGs), in order to allow evaluation of the adjuvant effect of the CAD treatment on the siRNA-mediated gene silencing.

Figure 2:
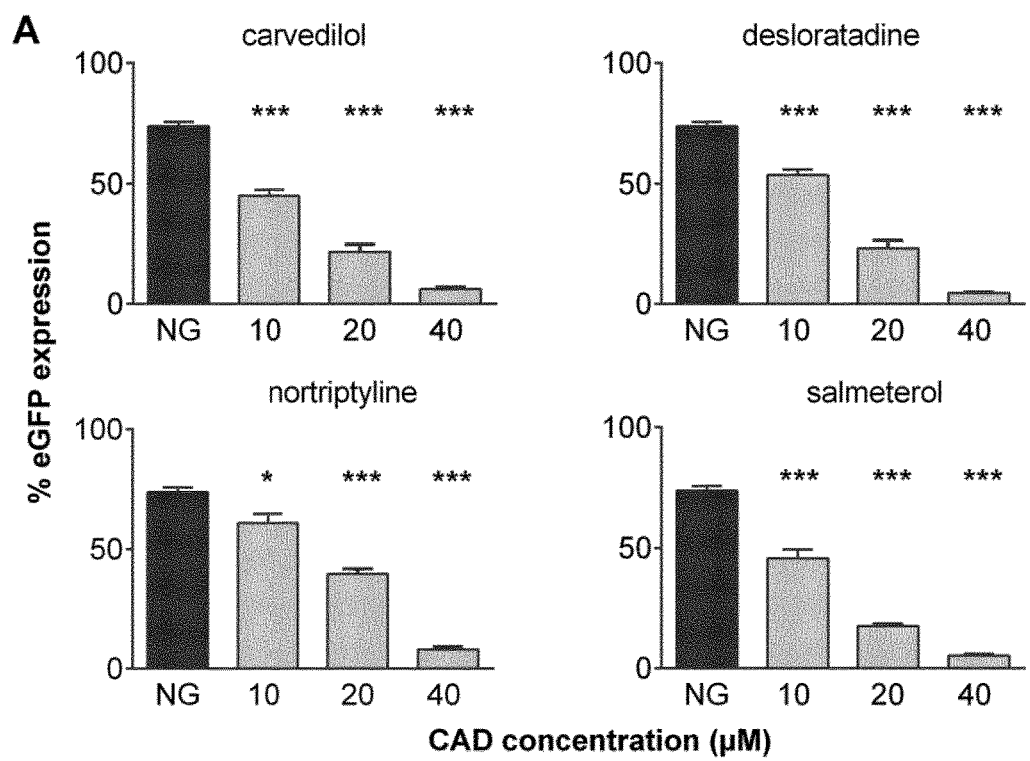
FIG. 2. Cationic amphiphilic drug (CAD) treatment significantly improves the silencing potential of siNGs in H1299_eGFP cells. (A) Transfection of H1299_eGFP cells with siNGs, loaded with a suboptimal amount of siRNA. Sequential carvedilol, desloratadine, nortriptyline and salmeterol addition caused a significant additional silencing of the stably expressed eGFP in a concentration dependent manner. All molecules induced nearly maximum eGFP gene silencing in case of 40 μM CAD addition in complete cell culture medium. (B) Combinations of desloratadine and nortriptyline evoked additive effects on eGFP silencing. (C) Comparison of eGFP knockdown between siNGs and lipofectamine® RNAiMAX. (D) Dextrometorphan does not influence gene silencing in the same dose range under identical experimental conditions. (E) Chloroquine enhances gene silencing to a similar extent as the initial molecules tested. The eGFP expression of the cells treated with eGFP-targeting siRNA (siEGFP) was normalized to the expression of cells treated with control siRNA (siCTRL). Data are represented as mean±the standard error of the mean (SEM) for minimum three independent biological replicates. Statistical significance, with respect to NG transfection alone (*), is indicated when appropriate (* $p<0.05$,  $p<0.01$, * $p<0.005$). Statistical significance between NG+40 μM DL and Lipofectamine® RNAiMAX is indicated when appropriate (xxx $p<0.005$). (NG=siNG transfection without sequential adjuvant treatment, DL=desloratadine, NT=nortriptyline, DX=dextromethorphan, CLQ=chloroquine).

In line with earlier reports, the siNGs were efficiently internalized by the H1299 cells (data not shown) and induced ~25% eGFP silencing under the given experimental conditions (FIG. 2A). Notably, the sequential treatment by each compound markedly improved the silencing potential of the internalized siNGs in a similar concentration-dependent fashion (FIG. 2A, FIG. 1). Compared to the siNGs alone, the lowest CAD concentration (10 µM) induced a significant increase in eGFP silencing and almost complete gene silencing was reached at 40 µM. When a combination of CADs was applied, additive effects on gene silencing were observed and no significant differences could be detected between the combination of DL and NT or double the concentration of both compounds (FIG. 2B).

The silencing potential of this approach was furthermore compared to the gold standard transfection reagent for siRNA delivery, i.e. Lipofectamine® RNAiMAX. When the latter is applied according to the manufacturer's guidelines (5 pmol siRNA per well) nearly complete gene silencing was obtained (FIG. 2C). In turn, when the lipoplexes were diluted to obtain a similar siRNA concentration per well as with the siNGs (0.6 pmol siRNA/well 2 nM siRNA) 55% gene silencing was obtained (FIG. 2C). Hence, Lipofectamine® RNAiMAX outperformed the suboptimal siNG transfection whereas the silencing obtained upon a sequential CAD treatment to siNG transfected cells clearly provided the best result.

In turn, not all CADs were active in the same dose range. For instance, 10-fold higher concentrations of dextromethorphan were required to obtain similar effects (FIG. 2D) and substantially lower concentrations were required of the compound terfenadine (FIG. 3).

Finally, in a positive control experiment, the sequential addition of the state-of-the-art endosomal escape enhancer chloroquine (CLQ) was investigated. CLQ improves the silencing potential of the siNGs to a similar extent as the first four molecules tested (FIG. 2E).

2. CAD Treatment Affects Cell Viability to a Minor Extent

Figure 4:
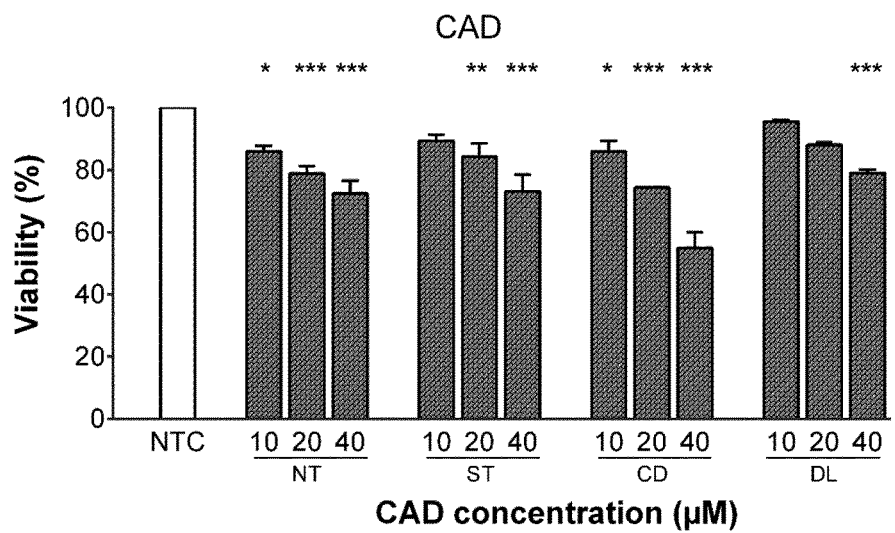
FIG. 4. Cell viability of the H1299_eGFP cells following (A) CAD treatment alone or (B) sequential to siNG transfection. Data reflect the mean±SEM (n=3, independent experiments) and statistical significance is indicated when appropriate (* $p<0.05$,  $p<0.01$, * $p<0.005$). In (B) the black * represent significant variations relative to the untreated control (NTC), whereas the grey * resemble significant variations with respect to the cells transfected with siCTRL-loaded NGs. (NG=nanogels, NT=nortriptyline, ST=salmeterol, CD=carvedilol, DL=desloratadine).
Figure 4:
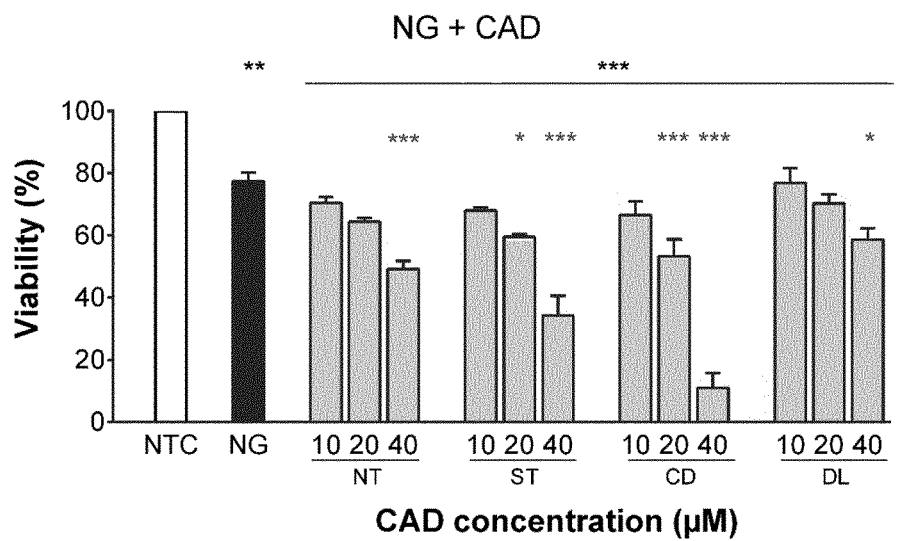

Subsequently, we evaluated the impact on cell viability of the CAD treatment alone or sequential to the siNG transfection. From FIG. 4A, which shows the viability (%) following CAD treatment alone, it is clear that the CADs were overall well tolerated in the applied concentration range, with DL and CD being the least and most cytotoxic, respectively. The NG transfection reduced the cell viability to ~80% (FIG. 4B). Of note, none of the CADs induced significant additional cytotoxicity compared to the siNGs alone at a concentration of 10 µM (FIG. 4B). For both ST and CD, significant additional cytotoxicity was detected starting from 20 µM while this was only the case for 40 µM NT or DL. Of note, only for ST and CD did the cytotoxicity observed at 40 µM exceed the sum of the effects from each separate component. Again, DL was best tolerated since ~60% of the transfected cells subsequently treated with 40 µM DL remained viable. Hence, DL induced the strongest enhancement of eGFP silencing with the lowest impact on cell viability.

3. Desloratadine Improves the Cytosolic Delivery of Macromolecules

We hypothesized that the sequential CAD treatment improved the siNG silencing potential by facilitating the transfer of the endo-lysosomally accumulated siRNA to the cytosol, through the induction of lysosomal membrane permeabilization (LMP). To evaluate if the CAD treatment improved escape into the cytosol through the induction of LMP, we assessed the CAD-mediated release of endocytosed 10 kDA FITC-labeled dextrans (FDs). In case of LMP, the cytoplasm is diffusely stained following FD leakage in contrast to the typical punctate pattern indicative of lysosomal sequestration.

As expected, the punctate pattern was observed in the bulk of the untreated cells, with a diffuse labeling only detected in ~2% of the cells (Table 3). Upon DL adjuvant treatment, we observed a concentration dependent increase in the % of cells with a diffuse cytosolic FD labeling, reaching up to ~26% following 40 µM DL treatment.

Subsequently, we confirmed the increased release for the selected nanogel carrier by applying NGs loaded with Cy5-labeled oligonucleotides. Upon release into the cytosol, the latter translocate to the nucleus and can thus be applied as an indicator for endosomal escape (Rehman Z., 2013). In only ~1% of the transfected cells oligonucleotides could be detected in the nuclei. In contrast, when cells were additionally treated with 40 µM DL, positive nuclei were detected in ~30% of the cells (Table 3). Taken together, these data suggest that CAD treatment can induce cytosolic release of macromolecules and oligonucleotides from the endo-lysosomal compartment, potentially through the induction of LMP.

TABLE 3

% of cells with a diffuse FITC-dextran labeling or oligonucleotide positive nuclei as a consequence of escape from the endo-lysosomal compartment.

|  | Cells with diffuse FITC-dextran labeling | Oligonucleotide positive nuclei |
| --- | --- | --- |
| No adjuvant | 2% | 1% |
| +40 µM DL | 26% | 30% |

4. The Lysosomal Compartment is Affected by CAD Treatment

The data presented thus far suggest that release into the cytosol of siRNA delivered by siNGs can be boosted by CAD treatment, likely through LMP induction by the latter. Prompted by these observations, we examined the impact of CAD treatment on the lysosomes of siNG transfected cells in more detail. Hereto, the organelles were labeled with the lysosomotropic dye LysoTracker® Deep Red (LDR) to allow quantification of the total volume of the lysosomal compartment.

Figure 5:
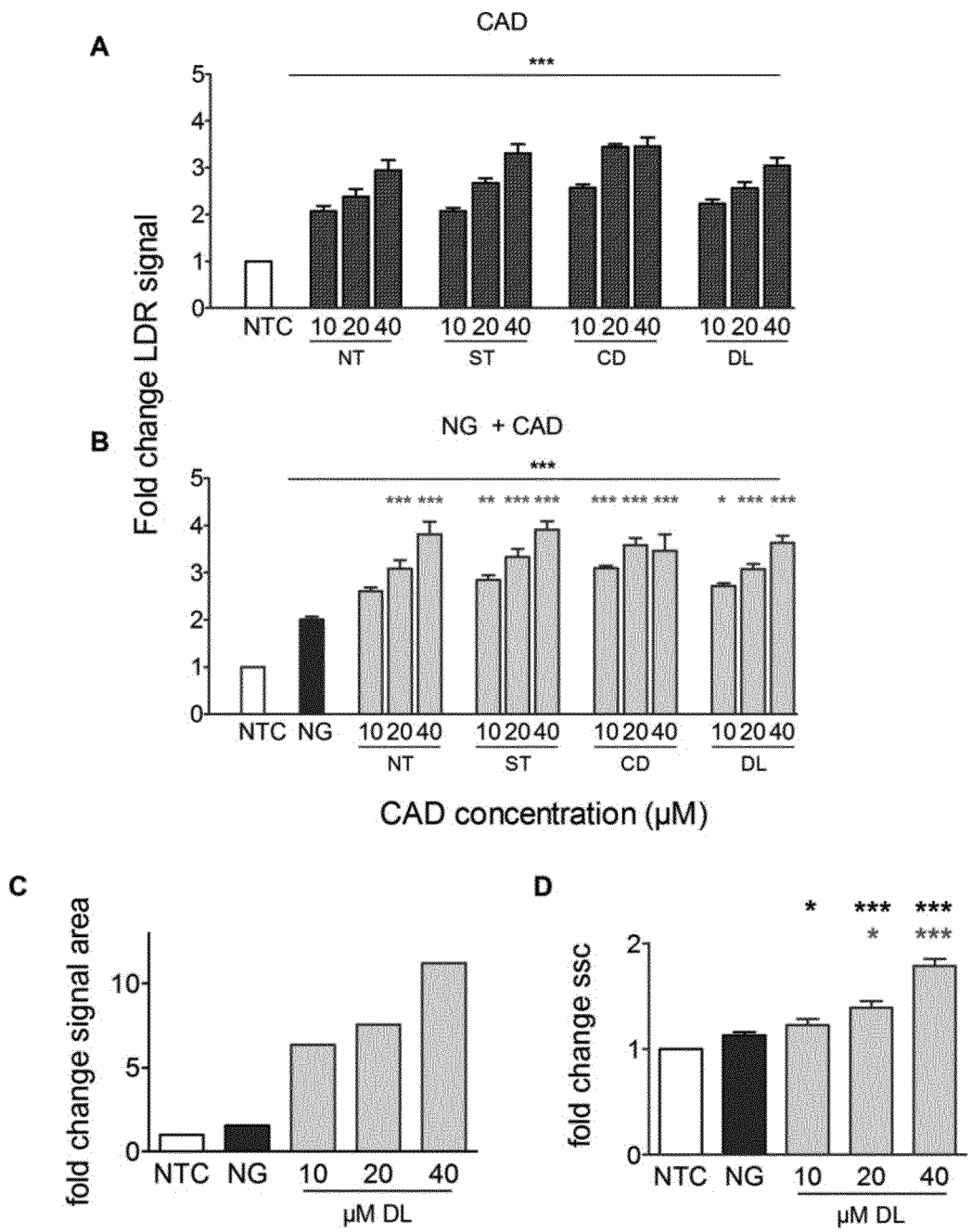
FIG. 5. Fold change in LysoTracker® Deep Red (LDR) signal measured via flow cytometry for cells (A) treated only with the CADs or (B) the combination of siNGs and CADs. (C) Fold increase in Lysotracker® signal area relative to the untreated control quantified from the confocal images for siNG transfected cells with and without DL. (D) Fold change in side scatter induced by siNG transfection or sequential treatment with DL. Data are represented as the mean±SEM (n=3). When appropriate, statistical significance with reference to the untreated control or siNG transfected cells is indicated in black and grey, respectively (* $p<0.05$,  $p<0.001$, * $p<0.005$). (NTC=not treated control, NG=nanogels, NT=nortriptyline, ST=salmeterol, CD=carvedilol, DL=desloratadine; FSC=forward scatter, SSC=side scatter).

FIG. 5A shows that all four CADs evoked a similar significant concentration-dependent signal increase compared to the untreated cells, as measured by flow cytometry. In addition, siNGs transfection alone caused a significant 2-fold signal raise with respect to the untreated control (FIG. 5B). Importantly, upon sequential CAD treatment the signal was additionally significantly elevated compared to the siNG-transfected cells for all CADs in nearly all concentrations.

These observations could visually be confirmed by confocal microscopy following labeling of the lysosomes with LysoTracker® Red. siNG endocytosis can explain the two-fold increase LDR signal for NG-transfected cells, as we witnessed an elevation in the number of labeled lysosomes without alterations in their appearance (results not shown). In turn, the additional signal increase upon sequential CAD treatment coincided with enlargement of the labeled vesicles, which was confirmed by quantification of the Lysotracker signal area (FIG. 5C). Notably, a very similar trend was obtained when quantifying the Lysotracker signal intensity (results not shown).

Figure 6:
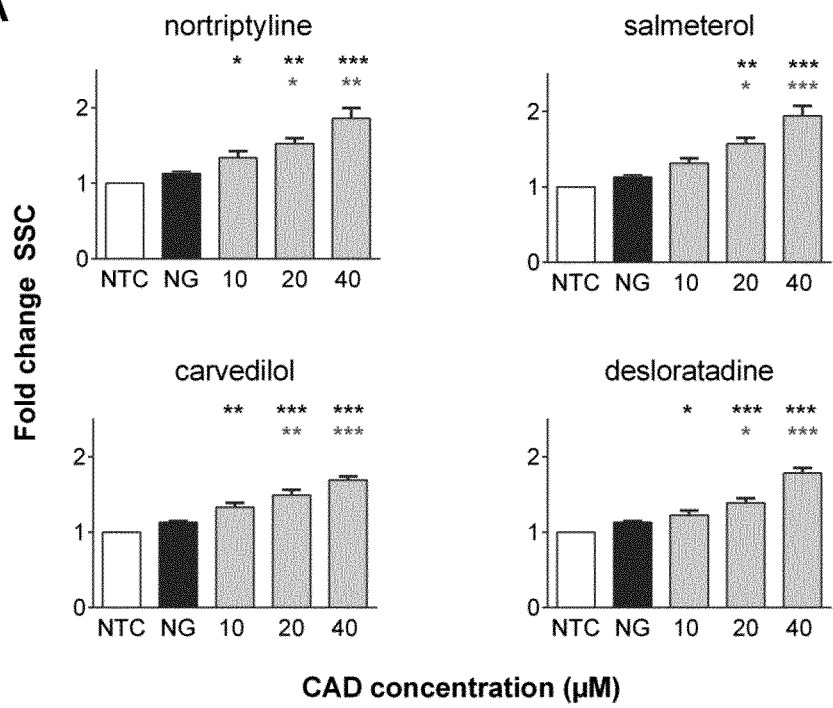
FIG. 6. (A) Fold increase in side scatter (SSC) with respect to the untreated control by siNG transfection of H1299_eGFP cells alone or with additional CAD treatment. Data are represented as the mean±SEM (n=3) and statistical significance is indicated when appropriate in black with reference to the untreated cells and in grey with respect to the siNG-transfected cells (* $p<0.05$,  $p<0.001$, * $p<0.005$). (NTC=not treated control, NG=nanogels). (B) Fold increase of the SSC signal upon siNG transfection of H1299_eGFP cells either or not followed by treatment with 10, 20 or 40 μM DL or NT or their combination. Data are represented as the mean±SEM (n=3) and statistical significance with reference to the untreated control is indicated when appropriate (* $p<0.05$,  $p<0.01$, * $p<0.005$). (NTC=not treated control, NG=nanogels, DL=desloratadine, NT=nortriptyline). (C) Fold change of the SSC signal upon siNG transfection of H1299_eGFP cells in combination with dextromethorphan treatment (10, 20, 40, 80, 120, 160 or 200 μM). Data are represented as the mean±SEM (n=3) and statistical significance with reference to the untreated control is indicated when appropriate (* $p<0.05$, *** $p<0.005$). (NTC=not treated control, NG=nanogels, DX=dextrometorphan).
Figure 6:
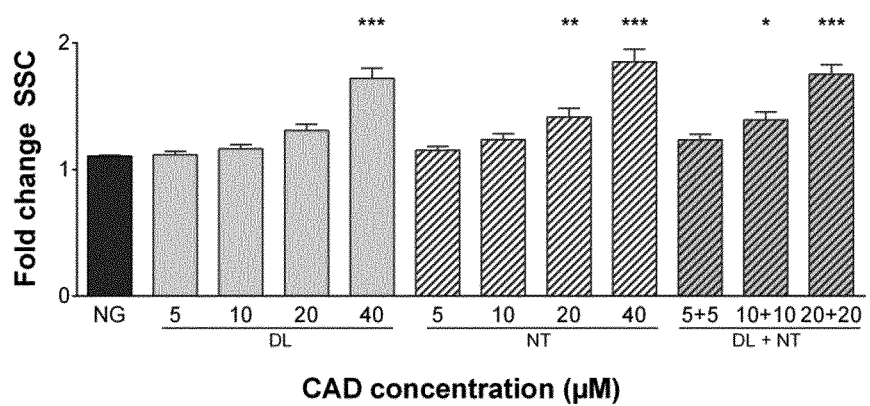
Figure 6:
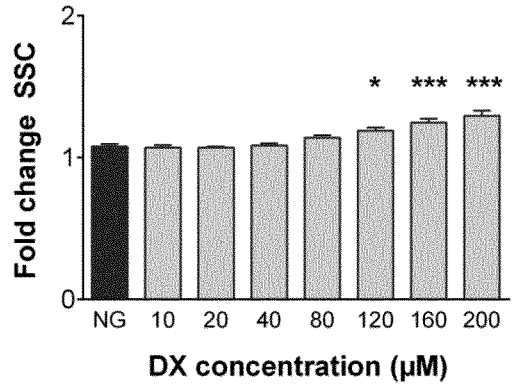

Finally, this CAD-induced lysosomal swelling in turn increased the cellular granularity, which could be verified by the analysis of the side scatter (SSC) signal (FIG. 5D). Upon NG transfection, a minor shift towards higher SSC values could be noted and this trend continued with mounting CAD concentrations (data not shown). Indeed, for 40 µM DL a clear shift of the cell population resulted in a 1.8-fold increase in the SSC signal (data not shown). Strikingly, similar trends were once again obtained for NT, ST and CD (FIG. 6A). With reference to the NG-transfected cells, all CADs evoked a significant increase in SSC starting from 20 µM. The combination of CADs in turn resulted in additive SSC increases and no significant variations were detected between the single compounds and the combination of half of their doses (FIG. 6B). According to dextromethorphan's effect on gene silencing, only higher doses (>80 µM) significantly augmented the SSC signal, although to a limited extent compared to the other molecules tested (FIG. 6C).

Taken together, we found CADs to induce enlargement of the lysosomal compartment, which coincided with enhanced siRNA-mediated silencing. Thus, we speculate that the CADs induced lysosomal swelling and minor LMP, to allow siRNA release.

5. CADs Induce a Lysosomal Storage Disease-Like Phenotype

Thus far we have shown that CAD treatment markedly improves siNG-mediated gene silencing, which is correlated to an enlargement of the lysosomal compartment combined with enhanced siRNA release from the lysosomes, presumably due to minor LMP. Quantification of the signal intensity of the phospholipidosis detection reagent LipidTOX™ Red (FIG. 7A) reveals that DL treatment also upregulates the presence of phospholipids in a concentration dependent fashion. Furthermore, only higher doses of dextromethorphan, a CAD of which also higher doses are required to influence gene silencing, clearly induce phospholipid accumulation.

Lysosomal swelling is a general phenotypical feature of lysosomal storage disorders (te Vruchte et al., 2014) Besides general PLD induction, several CADs have been shown to induce a Niemann-Pick disease (NPD) phenotype (Shoemaker et al., PloS One, 2013). NPD is a lysosomal storage disorder caused by either a genetic defect in the acid sphingomyelinase enzyme (ASM, NPD type A) or a depletion of the cholesterol transport protein NPC1 (NPD type C). Both NPD type A and C present a similar phenotype that is characterized by enlarged lysosomes due to the accumulation of phospholipids, such as cholesterol and (glyco-) sphingolipids, including sphingomyelin (SM) (Kirkegaard et al., Nature, 2010) (Petersen et al., 2013) (Funk et al., Mol. Pharm., 2012).

Figure 7:
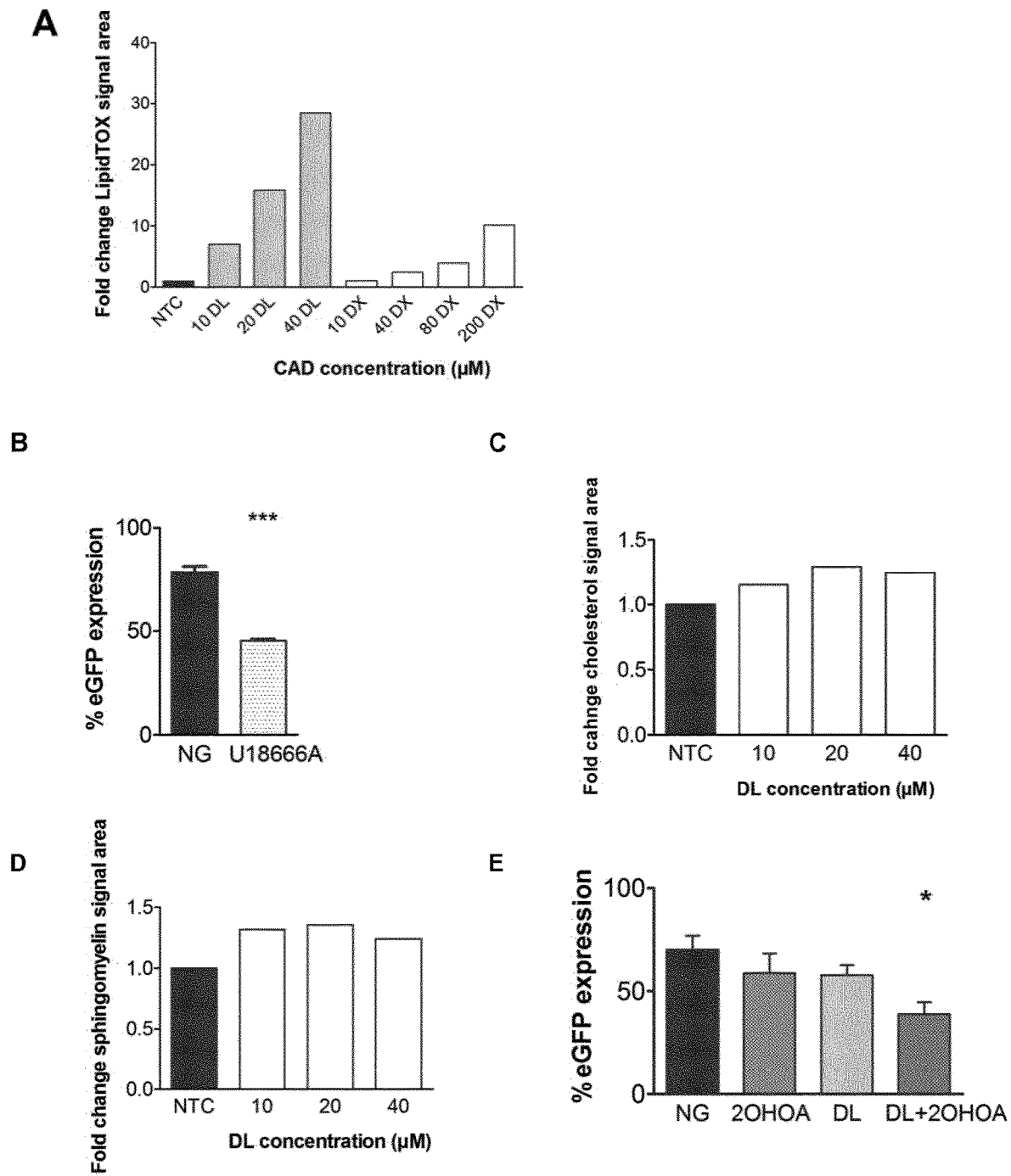
FIG. 7. (A) Augmentation of the LipidTOX™ red phospholipidosis detection reagent by desloratadine and dextromethorphan treatment. (B) The eGFP silencing in H1299_eGFP cells induced by adjuvant treatment with 30 μM U18666A compared to siNG transfection alone. (C) Fold increase in cholesterol signal area relative to the total cell area as determined following cholesterol labeling with filipin. (D) Fold increase in sphingomyelin signal area relative to the total cell area as determined following sphingomyelin labeling with lysenin. The signal increases as a function of the desloratadine concentration. (E) The % eGFP expression following transfection with the siNGs alone or in combination with adjuvant treatment with 300 μM 2OHOA, 10 μM DL or the combination of both. The eGFP expression of the cells treated with eGFP-targeting siRNA (siEGFP) was normalized to the expression of cells treated with control siRNA (siCTRL). Data are represented as the mean±SEM (n=3) and statistical significance is indicated when appropriate (* p<0.05, ** p<0.005) (NG=nanogels, DL=desloratadine, FSC=forward scatter, SSC=side scatter, DL=desloratadine, DX=dextromethorphan, 2OHOA=2-hydroxy oleic acid).

To experimentally confirm whether the induction of a NPD phenotype enhances siRNA mediated gene silencing we first compared the CAD adjuvant effect on siNG-mediated gene silencing to that of U18666A, an often applied small molecular inducer of the NPD phenotype. Compared to siNG-transfected cells sequentially treated with 40 µM DL, the cell granularity was augmented to an even greater extent in case of 30 µM U18666A adjuvant treatment, with a 2-fold increase in SSC signal compared to 1.8-fold for the former (data not shown). Moreover, U18666A clearly improved siNG-mediated gene silencing (FIG. 7B), albeit that the CADs included in this study (FIG. 2A) were more potent adjuvants under identical experimental conditions. Since both the CADs and U18666A induced a similar phenotype and NPD is correlated to cholesterol accumulation in the lysosomes, we quantified the cholesterol accumulation following siNG transfection and sequential CAD treatment (FIG. 7C). Upon DL treatment, an increase in the signal area relative to the total cell area could be noted. Notably, this cholesterol accumulation corresponds to that obtained with U18666A treatment and correlates well with our results on lysosomal swelling. In addition, we observed a similar accumulation of SM upon CAD treatment (FIG. 7D), corroborating that the CADs negatively influence the ASM activity and cause SM accumulation. Hence, the lysosomal swelling could presumably be attributed to lipid accumulation through the induction of a NPD-type A phenotype rather than osmotic swelling. To confirm whether the interference with the SM metabolism contributed to the enhanced siNG-mediated gene silencing, a combined treatment of 10 µM DL and 300 µM 2-hydroxy oleic acid (2OHOA), a known activator of the SM synthetase, was subsequently tested. The additive effect of 2-OHOA on the obtained gene silencing indeed suggests an involvement of lysosomal SM accumulation in the LMP and cytosolic siRNA delivery (FIG. 7E).

6. The Impact of a Reduced Incubation Period and Multiple DL Treatments

Figure 8:
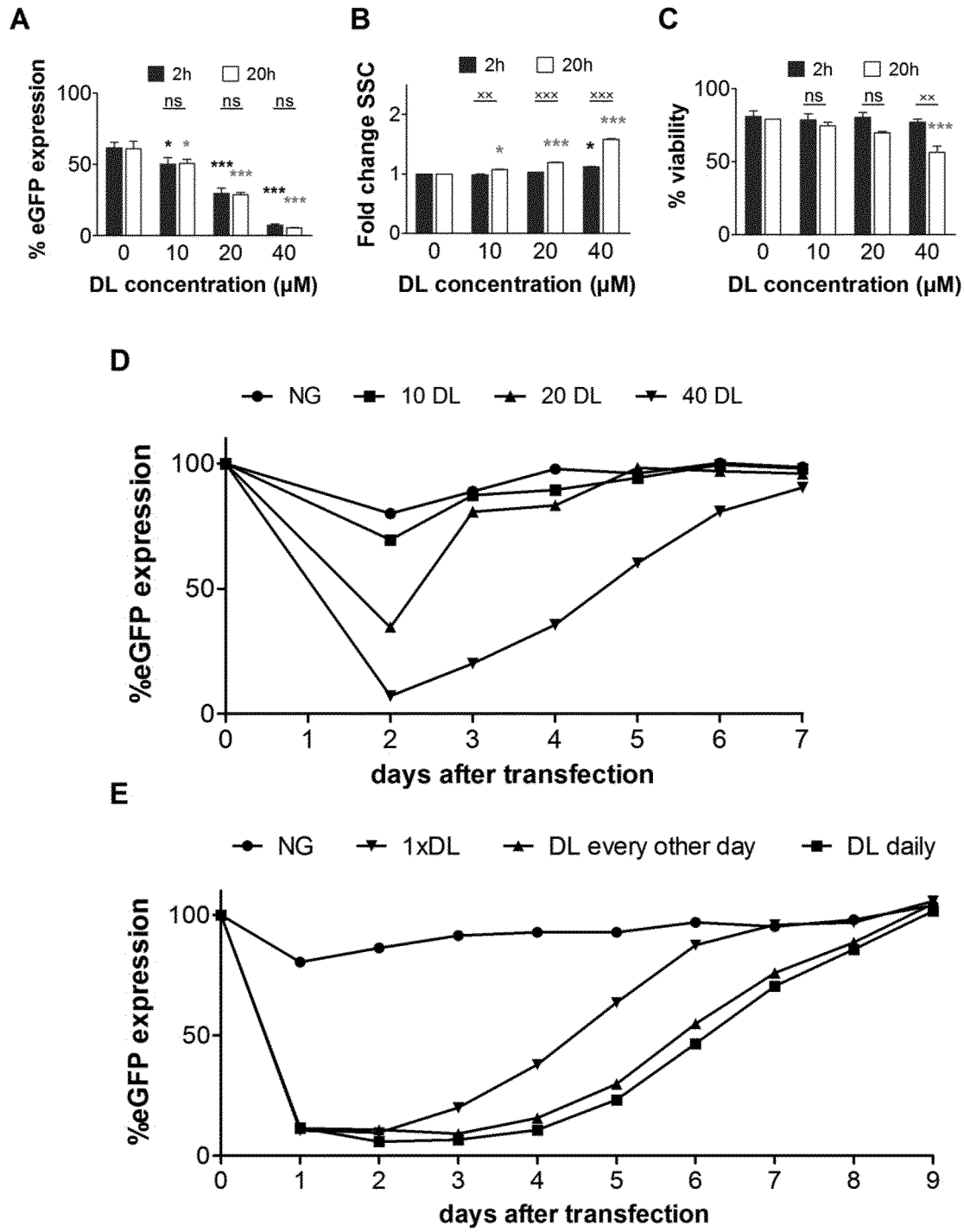
FIG. 8. (A) The % eGFP expression following transfection of H1299_eGFP cells with the siNGs alone or in combination with 2 h or 20 h DL treatment. (B) Fold change in side scatter (SSC) induced by siNG transfection or sequential treatment with siNGs and 2 h or 20 h DL. (C) % viable cells following siNG transfection either or not combined with 2 h or 20 h DL treatment. (D) Kinetics of eGFP knockdown in cells transfected with siNGs (circle) and treated a single time with 10 (square), 20 (upwards triangle) or 40 µM (downwards triangle) DL. (E) Kinetics of eGFP knockdown in cells transfected with siNGs (circle) and treated a single time with 40 µM DL (downwards triangle), daily (square) or every other day (upwards triangle). Data are represented as mean±SEM (n=3) and statistical significance is indicated when appropriate by black * when referring to the untreated control and grey * when compared to siNG transfected cells (* p<0.05,  p<0.001, * p<0.005). Finally, statistical significance between the 2 h and 20 h condition is indicated by the black x (xx p<0.01, xxx p<0.005). (NG=nanogels, DL=desloratadine).

In a subsequent set of experiments we evaluated whether the DL incubation time could be reduced from 20 hours to 2 hours. FIG. 8A shows that both a 2 h and 20 h incubation period improve siNG-mediated gene silencing to a similar extent. Of note, the SSC signal measured at the time of the eGFP readout is significantly lower in cells only treated 2 h with DL (FIG. 8B). Indeed, only 40 µM DL caused a significant though minor augmentation of the cellular granularity. This result suggests that the induced PLD phenotype is only transiently present and that the cellular phenotype is restored upon removal of the compound. Interestingly, a 2 h DL incubation period did not cause any additional cytotoxicity compared to the siNGs alone (FIG. 8C). Thus, the faster recovery from the PLD state possibly has a positive effect on cell viability.

Figure 9:
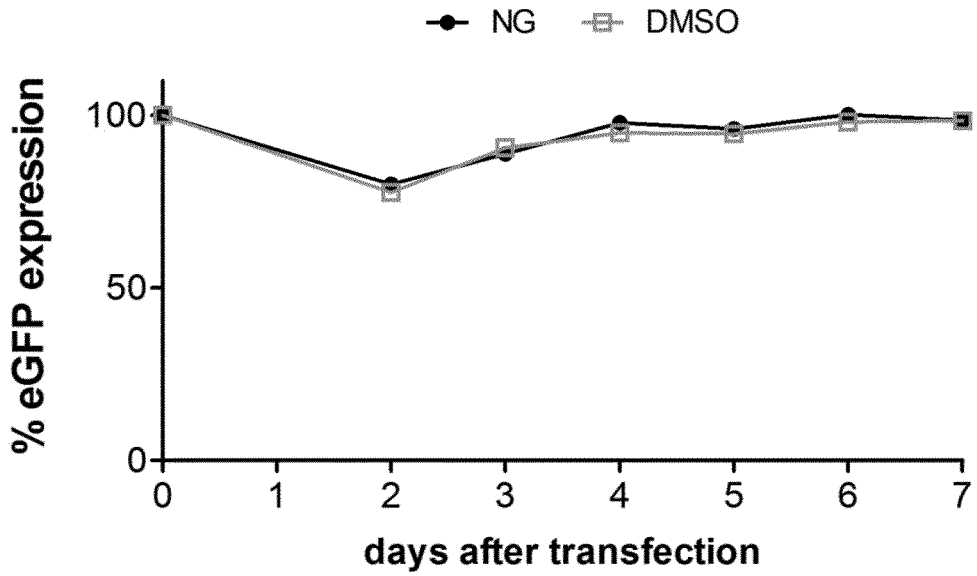
FIG. 9. Kinetics of eGFP silencing in cells transfected with siNGs (black) and a single time exposed to 0.16% DMSO in cell medium (grey).
Figure 10:
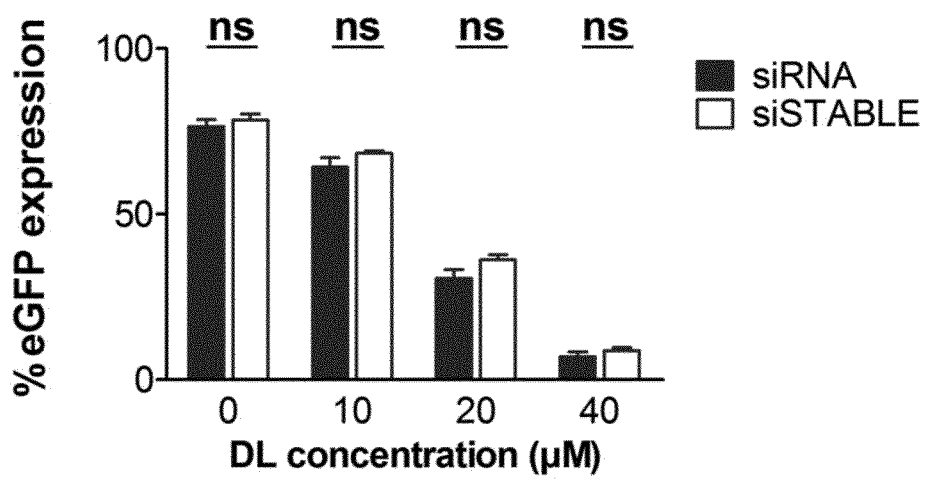
FIG. 10. % eGFP expression following NG-mediated siRNA delivery of unmodified siRNA (black) and nuclease-stabilized siRNA (siSTABLE, white) in combination with 10, 20 or 40 µM desloratadine (DL).

Next, we investigated whether DL treatment influenced the kinetics of the siNG-mediated gene silencing. Since the compounds are dissolved in DMSO, we first ensured that the presence of DMSO did not alter the eGFP expression over time (FIG. 9). A concentration dependent improvement of initial gene silencing was obtained in correspondence to previous results (FIG. 8D). At day 2 post transfection, maximum gene silencing levels were obtained in each condition and eGFP expression steadily increased starting from day 3. At day 7 expression reached 100% in all samples. Interestingly, siGLO release experiments showed that DL treatment did not induce release of all the lysosomally accumulated siRNA (data not shown). Hence, we hypothesized whether it would be feasible to induce additional siRNA release upon multiple DL treatments. Since we applied stabilized siRNA for this experiment to reduce possible lysosomal degradation, we first confirmed that we obtained similar silencing results with both siRNA molecules (FIG. 10). Most interestingly, we observed that additional siRNA could be released in the cytosol upon multiple 2 h DL treatments, which allowed to maintain the eGFP silencing over a prolonged period of time (FIG. 8E).

7. Confirmation with a Therapeutic siRNA Against PLK1

All previous experiments were performed on the eGFP reporter gene. To evaluate whether our approach also works in a therapeutic setting we applied siRNA against Polo Like Kinase 1 (PLK1). Reducing the expression of this kinase has been shown to halt the cell cycle and even induce apoptosis in cancer cells, especially in p53 null cancer cells, such as the applied H1299 cell line. To evaluate the PLK1 silencing we evaluated the effect on cell viability since both induction of cell cycle arrest or apoptosis would reduce the number of cells present compared to the untreated control.

Figure 11:
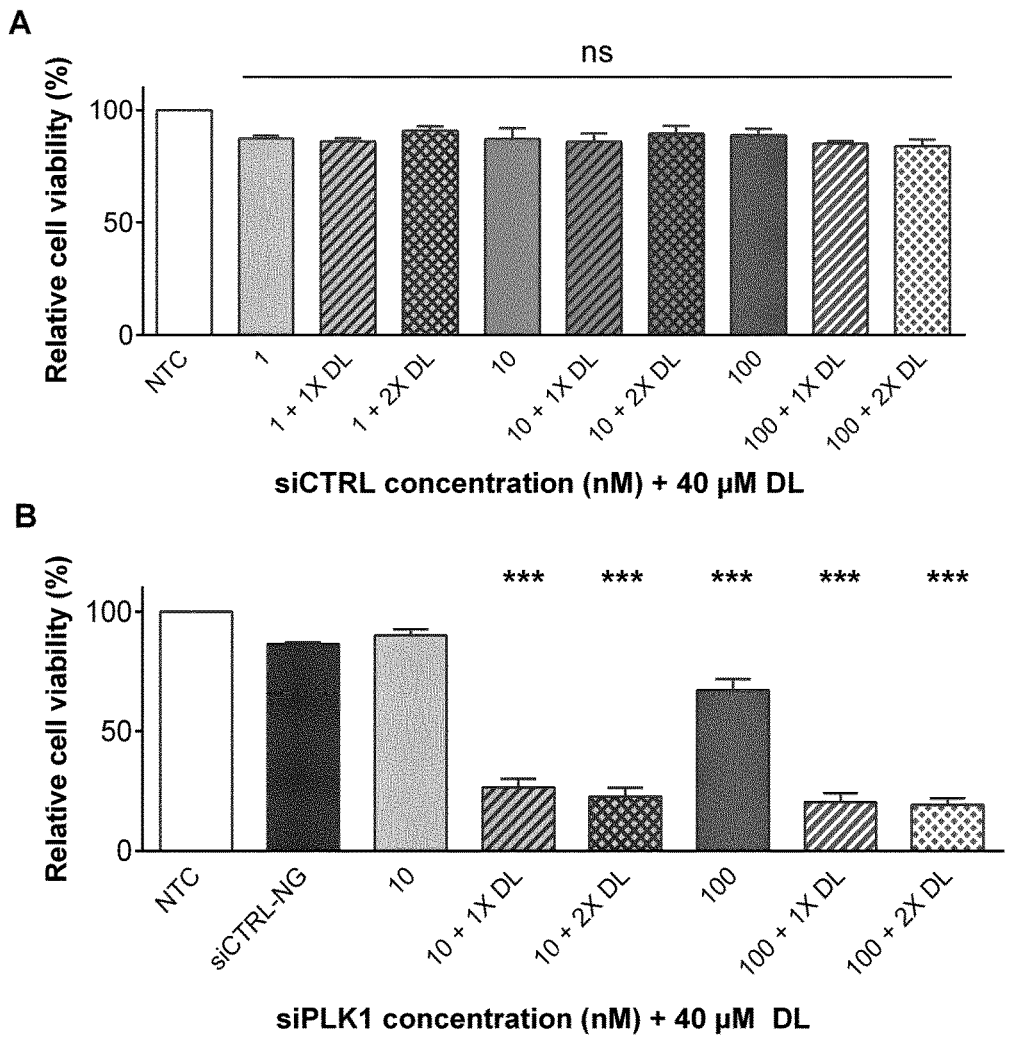
FIG. 11. (A) H1299_eGFP cell viability measured upon transfection with siCTRL-NGs. No significant variations in cell viability could be detected between the various treatment groups. (B) Relative H1299_eGFP cell viability indicative of PLK1 silencing for cells transfected with 10 or 100 nM siPLK1 and treated without DL or once or twice with 40 µM DL. A second DL treatment could not further improve the siPLK1 effect. Data are represented as the mean±SEM (n=3) and the statistical significance is indicated when appropriate. (ns=not significant; *** p<0.005). (PLK1=polo-like kinase 1, DL=desloratadine, NTC=not treated control).

The siNGs loaded with control siRNA reduced cell viability to approximately 80% in any condition tested, corroborating previous experiments. In addition, an increase in siCTRL dose or a single or two DL treatment(s) sequential to siCTRL-NG transfection did not affect cell viability (FIG. 11A). Therefore, effects observed with siPLK1 can solely be attributed to PLK1 silencing. Doses of 1 and 10 nM siPLK1 were not able to additionally affect cell viability, while 100 nM siPLK1 reduced the cell viability further to ~60% (FIG. 11B). Likewise, a single 40 µM DL treatment (2 h incubation) could reduce cell viability with only 1 nM siPLK1 to ~60% and a second treatment further reduced viability to ~50%, indicating the fold improvement of the adjuvant approach (data not shown). The most extensive adjuvant effect was observed for 10 nM siPLK1 where a maximal effect on cell viability reduction was obtained with a single 2-hour DL treatment (FIG. 11B).

Figure 12:
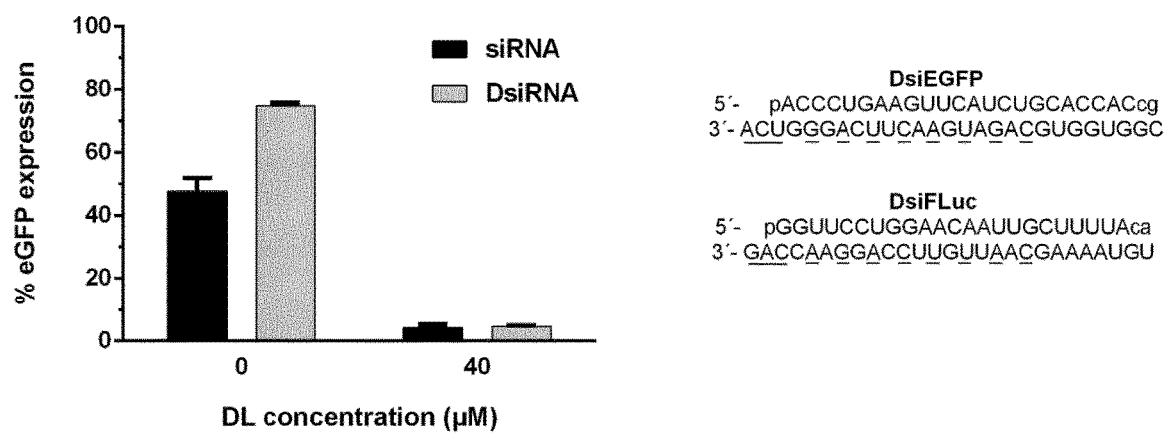
FIG. 12. Evaluation of gene silencing potential of NGs loaded with siRNA (black) or 25-27 mer Dicer-substrate siRNA (DsiRNA; grey) in H1299_eGFP cells upon sequential treatment with 40 µM DL during 20 hours. The experiments were performed with a fixed NG concentration (30 µg/mL) and siRNA/DsiRNA concentration (5 nM). The eGFP expression of the cells treated with eGFP-targeting siRNA or DsiRNA was normalized to the expression of cells treated with control siRNA or DsiRNA. siRNA targeting eGFP (siEGFP) and negative control siRNA (siCTRL) were purchased from Eurogentec. Sequences are illustrated in the section Materials and Methods. DsiRNA targeting eGFP (DsiEGFP—SEQ ID N° 13 and SEQ ID N° 14) or targeting firefly luciferase (DsiFLuc; used as negative control—SEQ ID N° 15 and SEQ ID N° 16), were obtained from IDT (Leuven, Belgium). The sequence is illustrated in the figure, whereby p denotes a phosphate residue, lower case letters are 2'-deoxyribonucleotides, capital letters are ribonucleotides and underlined capital letters are 2'-O-methylribonucleotides. The data are represented as mean±SD (n=3, technical replicates). DL=desloratadine.
Figure 13:
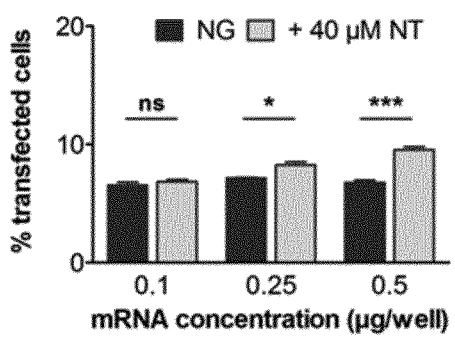
FIG. 13. (A) Table shows size and ζ-potential of NGs as a function of mRNA loading, determined by DLS (n=3, technical replicates). (B) Transfection efficiency in terms of the percentage of transfected H1299 cells and (C) the eGFP mean fluorescence intensity (MFI) of the transfected cells for mRNA-NG transfected cells alone (black) or combined with a 20 hours 40 µM NT treatment (grey). (D) Transfection efficiency in terms of the percentage of transfected cells and (E) the eGFP MFI of cells transfected with Lipofectamine™ messengerMAX™ (black) with or without 40 µM NT (grey). The data are represented as the mean±SEM for 3 technical replicates. Statistical significance is indicated when appropriate (ns=not significant, *p<0.05, ***p<0.005). NT=nortriptyline.
Figure 13:
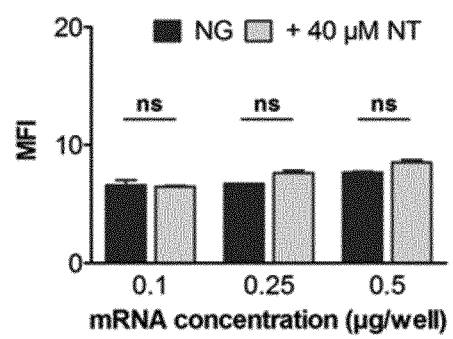
Figure 13:
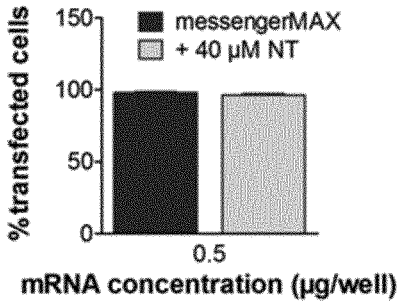
Figure 13:
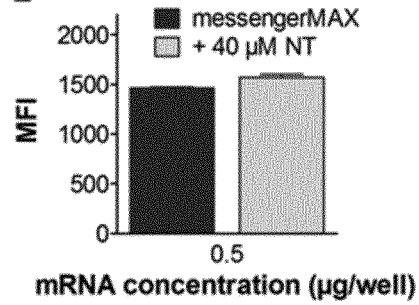

Of note, the delivery efficiency of siNGs loaded with the larger 25-27mer Dicer substrate siRNAs (DsiRNA, ~18 kDa) could also be promoted by sequential CAD incubation (FIG. 12), in contrast to eGFP-encoding mRNA (FIG. 13), implying that higher adjuvant concentrations and more extensive LMP might be required for cytosolic delivery of larger nucleic acid therapeutics.

Figure 14:
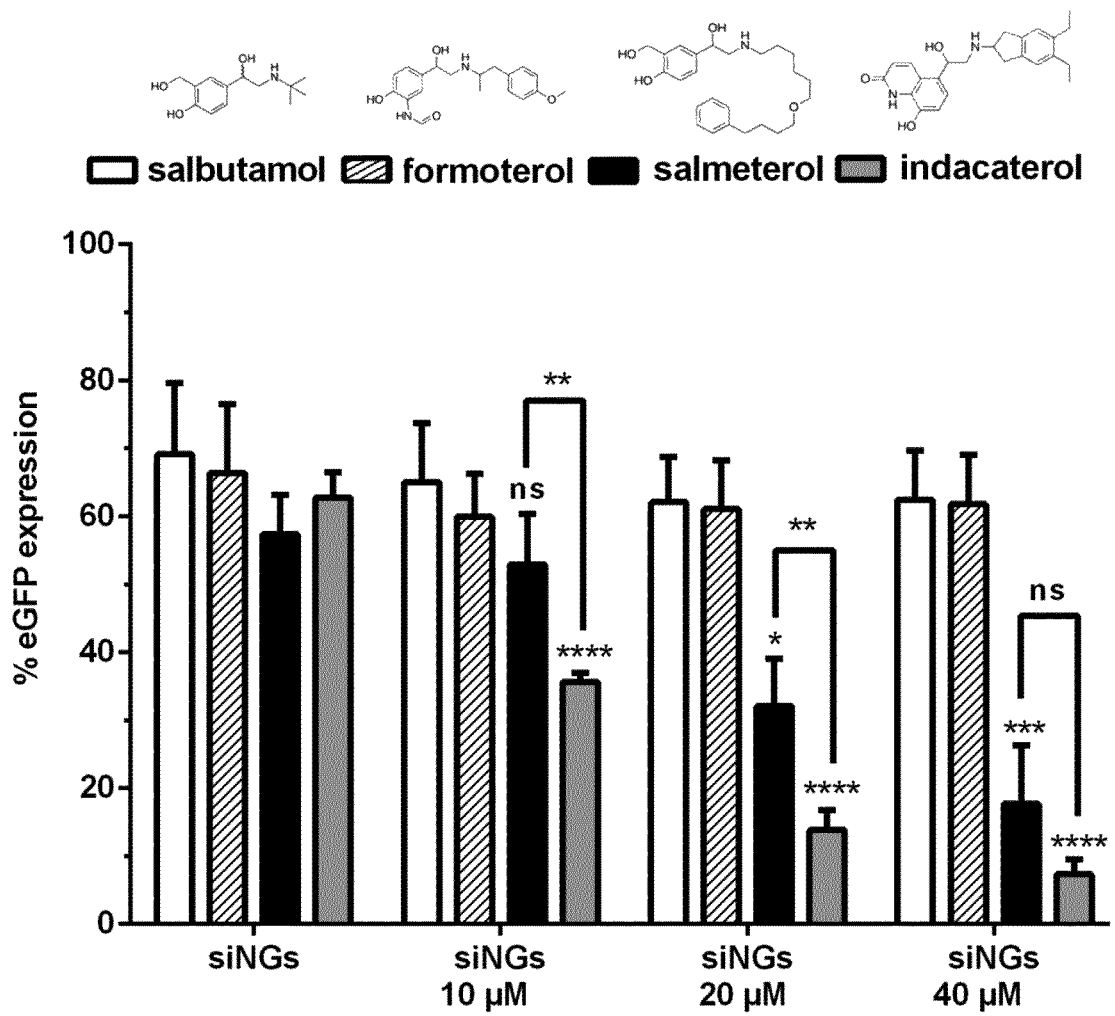
FIG. 14. Adjuvant effect on cellular siRNA delivery in H1299_eGFP cells, mediated via siNGs. The siNGs were incubated with the cells for 4 hours to allow endocytic uptake, followed by a 20 hour post-incubation with different concentrations of the test compound, as indicated in the graph. The eGFP expression, as quantified by flow cytometry, of cells treated with eGFP targeting siRNA (siEGFP) was normalized to the expression of cells treated with control siRNA (siCTRL). All experiments were performed with a fixed NG concentration (30 µg/mL) and siRNA concentration (2 nM) (n=3, 3 independent repeats; * p≤0.05,  p≤0.01, * p≤0.001, **** p≤0.0001). All data are presented as mean±standard deviation (SD). Statistical analysis was performed via one-way ANOVA followed by a Bonferroni's multiple comparison test, using GraphPad Prism software version 6.

Next to salmeterol, also other β2 agonists with comparable pKa were evaluated for their siRNA delivery promoting effect. Interestingly, only (ultra-)long acting β2 agonists with a log P>3, such as salmeterol and indacaterol, significantly improve cellular siRNA delivery. In contrast, short acting (salbutamol) and long-acting β2 agonists (formoterol) with a log P<3, do not qualify as siRNA delivery enhancers under identical experimental conditions (FIG. 14). As such, these data again demonstrate that the delivery promoting effect is independent of the compound's pharmacological activity and emphasizes the importance of the compounds hydrophobicity.

Figure 15:
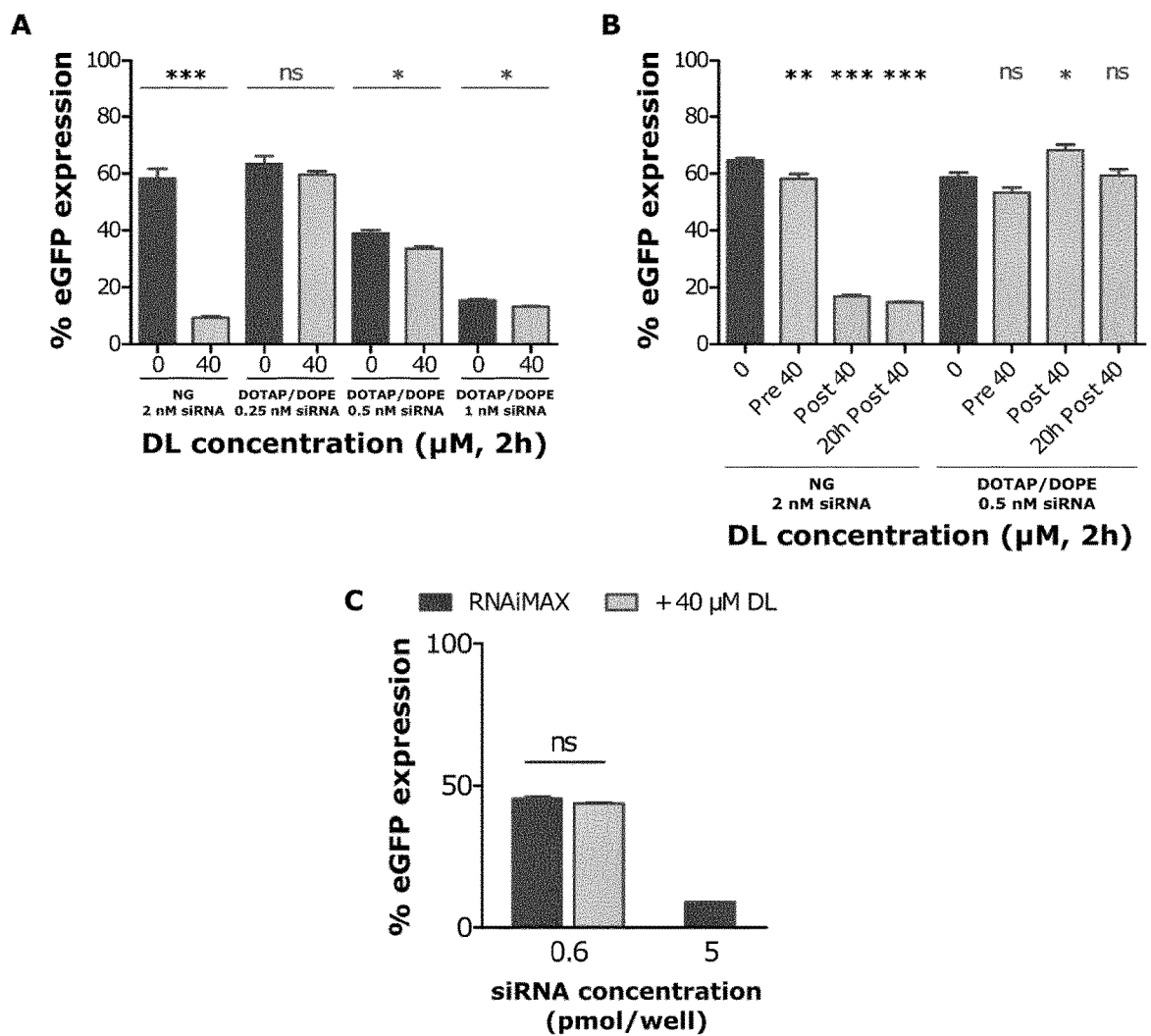
FIG. 15. Sequential desloratadine treatment significantly improves the silencing potential of siNGs, but not of siRNA-loaded DOTAP-DOPE LPS or RNAiMAX LPS, in H1299_eGFP cells. (A) The influence of 2 hours sequential adjuvant treatment with 40 µM desloratadine (DL) on the transfection efficiency of siNGs (complexing 2 nM siRNA) or siRNA-loaded DOTAP-DOPE LPS (complexing varying siRNA concentrations). (B) Impact on siNG and DOTAP-DOPE LPS mediated eGFP silencing of a 2-hour DL pre-incubation (Pre), 2-hour DL treatment immediately after (Post) or 2-hour DL treatment 20 hours after transfection (20 h Post), (C) Impact of a 2-hour DL treatment on eGFP expression upon transfection with Lipofectamine® RNAiMAX, complexing 0.6 pmol siRNA. Data are represented as the mean±the standard error of the mean (SEM) for 3 technical replicates within a single biological replicate. In (A) and (B) the black * represent significant variations relative to the cells transfected with siNGs, whereas the grey * resemble significant variations with respect to the cells transfected with siRNA-loaded DOTAP-DOPE LPS (* p<0.05,  p<0.01, * p<0.005). In (C) statistical significance between Lipofectamine® RNAiMAX with or without adjuvant treatment is indicated when appropriate.

Moreover, it was verified that desloratadine, although it significantly improved the cellular delivery potential of siNGs and clearly enhanced the cellular granularity, was not able to enhance cytosolic siRNA delivery mediated via cationic liposomes, as exemplified by DOTAP:DOPE (50:50 mol %) liposomes or lipofectamine® RNAiMAX liposomes (FIG. 15).

Finally, we screened the NIH Clinical Compound Collection (700 compounds) for siRNA delivery enhancers, again using the transfected H1299_eGFP cells as a model. All molecules were tested at a concentration of 20 µM in complete cell culture medium with a cell incubation time set at 20 h.

The data provided herein, together with the screen, identified the compounds listed in Table 1 as delivery promoting compounds and are highly suitable for use in the methods, combinations and compositions of the present invention.

Although the clinical translation of siRNA based therapeutics faces multiple challenges, endo-lysosomal sequestration is regarded as the major bottleneck at the cellular level. Hence, many groups have and are still evaluating methods to enhance endosomal escape. For example, material scientists have developed materials, which should aid the escape from the endosomal compartment into the cytosol. For instance, cationic polymers, such as polyethylenimine (PEI), are applied because of the ease of complexing negatively charged nucleic acids and the large buffering capacity. The latter is responsible for inducing an osmotic burst due to the proton sponge effect, thereby enabling nucleic acid release into the cytosol. Other examples are the use of fusogenic or lysogenic peptides, which respectively destabilize or lyse the membrane of endocytic organelles to create pores through which escape occurs. In order to avoid degradation of the particle and its drug payload in the lysosomes, the effects of such enhancers should occur as soon as possible after uptake. Consequently, the time frame where such endosomal escape strategies can be of benefit is rather narrow, as several studies have reported nanocarriers to be trafficked to the lysosomes within one hour after uptake. In stark contrast to this governing paradigm, in which the lysosomes are considered a dead-end for nanomedicines, we rather propose to exploit instead of avoid the lysosomes to enhance cytosolic delivery. To target the lysosomes could entail additional advantages. For one thing, the time frame over which the cytosolic release of the drug payload could be induced would be broadened. Also, if a single adjuvant treatment would not enable release of the complete internalized dose, the lysosomes could become a depot for cytosolic delivery upon consequent adjuvant treatments, which we have demonstrated in the present invention using nuclease stabilized siRNAs.

Here, we set out to enhance the release of the siRNA entrapped in the lysosomes by the sequential treatment with small molecular adjuvants, which is demonstrated as an important dose-sparing strategy. The latter can be important to reduce possible off-target effects of the siRNA treatment. The enhanced gene silencing was explained in terms of increased siRNA release from the lysosomal compartment due to adjuvant-mediated inhibition of ASM, leading to a transient induced PLD phenotype and non-lethal LMP.

In conclusion, we showed that adjuvant treatment clearly improved the silencing potential of siRNA-loaded NGs. The extent of the improvement varied in a concentration-dependent manner and almost complete knockdown was obtained for the highest adjuvant concentration tested. Remarkably, the additional adjuvant treatment only had a mild effect on cell viability. In addition, we show that the adjuvants described herein were able to enhance cytosolic delivery of siRNA through the escape from the lysosomal compartment. The lysosomes, where the adjuvants preferably accumulate, were affected by the adjuvant treatment as a concentration-dependent swelling was noted as well as the accumulation of both cholesterol and SM. This could be explained by the interference of the adjuvants with the SM metabolism as a consequence of their ASM inhibitory (FIASMA) activity. This accumulation, leading to an imbalance in lysosomal membrane lipid composition, subsequently caused the induction of limited LMP, thereby allowing the siRNA to be released into the cytosol. The method of the present invention can be broadly applicable toward therapeutic and diagnostic applications for distinct classes of membrane-impermeable agents.

REFERENCES

Aits, S.; Jäättelä, M.; Nylandsted, J. Methods for the quantification of lysosomal membrane permeabilization: a hallmark of lysosomal cell death. Methods Cell Biol. 2015, 126, 261-285.

De Backer, L.; Braeckmans, K.; Demeester, J.; De Smedt, S. C.; Raemdonck, K. The influence of natural pulmonary surfactant on the efficacy of siRNA-loaded dextran nanogels. Nanomedicine (Lond.) 2013, 8, 1625-1638.

Funk, R. S.; Krise, J. P. Cationic Amphiphilic Drugs Cause a Marked Expansion of Apparent Lysosomal Volume: Implications for an Intracellular Distribution-Based Drug Interaction. Mol. Pharm. 2012, 9, 1384-95.

Kirkegaard, T.; Roth, A. G.; Petersen, N. H.; Mahalka, A. K.; Olsen, O. D.; Moilanen, I.; Zylicz, A.; Knudsen, J.; Sandhoff, K.; Arenz, C., et al. Hsp70 Stabilizes Lysosomes and Reverts Niemann-Pick Disease-Associated Lysosomal Pathology. Nature 2010, 463, 549-53.

Kornhuber, J.; Tripal, P.; Reichel, M.; Terfloth, L.; Bleich, S.; Wiltfang, J.; Gulbins, E. Identification of new functional inhibitors of acid sphingomyelinase using a structure-property-activity relation model. J. Med. Chem. 2008, 51, 219-37.

Kornhuber, J.; Tripal, P.; Reichel, M.; Mühle, C.; Rhein, C.; Muehlbacher, M.; Groemer, T. W.; Gulbins, E. Functional Inhibitors of Acid Sphingomyelinase (FIASMAs): a novel pharmacological group of drugs with broad clinical applications. Cell Physiol. Biochem. 2010, 26, 9-20.

Petersen, N. H.; Olsen, O. D.; Groth-Pedersen, L.; Ellegaard, A. M.; Bilgin, M.; Redmer, S.; Ostenfeld, M. S.; Ulanet, D.; Dovmark, T. H.; Lonborg, A., et al. Transformation-Associated Changes in Sphingolipid Metabolism Sensitize Cells to Lysosomal Cell Death Induced by Inhibitors of Acid Sphingomyelinase. Cancer Cell 2013, 24, 379-93.

Rehman, Z. U.; Hoekstra, D.; Zuhorn, I. S. Mechanism of Polyplex- and Lipoplex-Mediated Delivery of Nucleic Acids: Real-Time Visualization of Transient Membrane Destabilization without Endosomal Lysis. ACS Nano 2013, 7, 3767-3777.

Shoemaker, C. J.; Schornberg, K. L.; Delos, S. E.; Scully, C.; Pajouhesh, H.; Olinger, G. G.; Johansen, L. M.; White, J. M. Multiple Cationic Amphiphiles Induce a Niemann-Pick C Phenotype and Inhibit Ebola Virus Entry and Infection. Plos One 2013, 8, e56265.

te Vruchte, D.; Speak, A. O.; Wallom, K. L.; Al Eisa, N.; Smith, D. A.; Hendriksz, C. J.; Simmons, L.; Lachmann, R. H.; Cousins, A.; Hartung, R., et al. Relative Acidic Compartment Volume as a Lysosomal Storage Disorder-Associated Biomarker. J. Clin. Invest. 2014, 124, 1320-1328.

Wishart D S, Knox C, Guo A C, Shrivastava S, Hassanali M, Stothard P, Chang Z, Woolsey J. DrugBank: a comprehensive resource for in silico drug discovery and exploration. Nucleic Acids Res. 2006 Jan. 1; 34.

The invention claimed is:

1. A combination comprising:
   a small non-coding RNA or antisense oligonucleotide,
   a cationic polymeric nanoparticle, and
   at least one cationic amphiphilic compound, wherein the at least one cationic amphiphilic compound has a molecular weight below 1000 g/mol, has a log P value of at least 3, and comprises one or more basic amines, wherein the conjugated acid of no more than one of the basic amines has a pKa of at least 5,
   and further wherein the at least one cationic amphiphilic compound is chosen from thiothixene, thioridazine hydrochloride, desloratadine, perphenazine, raloxifene hydrochloride, loperamide hydrochloride, nonyloxytryptamine hydrochloride, paroxetine maleate, clofazimine, fluoxetine hydrochloride, toremifene citrate, amiodarone hydrochloride, saquinavir mesylate, indatraline hydrochloride, duloxetine hydrochloride, clomipramine hydrochloride, clomipramine hydrochloride, salmeterol, mefloquine hydrochloride, lofepramine, imatinib mesylate, nelfinavir mesylate, miconazole nitrate, trifluoperazine hydrochloride, sertraline hydrochloride, carvedilol, aripiprazole, azelastine hydrochloride, SB 205607 dihydrobromide, econazole nitrate, amitriptyline hydrochloride, cyproheptadine hydrochloride, benproperine phosphate, dextromethorphan hydrobromide monohydrate, rimcazole dihydrochloride, clomifene citrate, imipramine hydrochloride, naltrindole hydrochloride hydrate, prochloperazine maleate, chlorpromazine hydrochloride, haloperidol hydrochloride, hydroxyzine pamoate, diphenoxylate hydrochloride, CGS 12066B dimaleate, amoxapine, desipramine hydrochloride, olanzapine, pizotyline maleate, naftopidil, verapamil hydrochloride, clozapine, promethazine hydrochloride, SKF 83566 hydrobromide, ketoconazole, nortriptyline hydrochloride, terfenadine, indacaterol maleate, a salt thereof or combinations thereof.

2. The combination according to claim 1, wherein the polymeric nanoparticle is coupled to or comprises the small non-coding RNA or antisense oligonucleotide.

3. The combination according to claim 1, wherein the combination further comprises a pharmaceutically acceptable excipient, carrier and/or diluent.

4. The combination according to claim 1, wherein the small non-coding RNA is a synthetic RNA, a labelled RNA, a small interfering RNA (siRNA), a Dicer-substrate siRNA (DsiRNA) or a microRNA (miRNA), or wherein the antisense oligonucleotide is RNA or DNA.

5. The combination according to claim 1, wherein the cationic amphiphilic compound is associated with, covalently coupled to, or incorporated in the polymeric nanoparticle.

6. The combination according to claim 1, wherein the polymeric nanoparticle coupled to or comprising a small non-coding RNA or antisense oligonucleotide is administered to a cell or subject prior, concurrent or after the administration of the at least one cationic amphiphilic compound to the cell or subject.

7. The combination according to claim 1, wherein the polymeric nanoparticle further comprises an imaging agent, a ligand or cell-trafficking agent.

8. The combination according to claim 1, wherein the cationic amphiphilic compound is chosen from terfenadine, nortriptyline, salmeterol, carvedilol, desloratadine or indacaterol, or a salt thereof.

9. The combination according to claim 1, wherein the cationic polymeric nanoparticle is a dextran nanogel.

10. A method for delivering small non-coding RNA or antisense oligonucleotide into the cytosol of a cell, the method comprising administering a combination comprising:
- a small non-coding RNA or antisense oligonucleotide,
- a cationic polymeric nanoparticle, and
- at least one cationic amphiphilic compound, wherein the at least one cationic amphiphilic compound has a molecular weight below 1000 g/mol, has a log P value of at least 3, and comprises one or more basic amines, wherein the conjugated acid of no more than one of the basic amines having a pKa of at least 5 to the cell or to a subject.

11. The method of claim 10, wherein the cationic amphiphilic compound is chosen from thiothixene, thioridazine hydrochloride, desloratadine, tamoxifen, perphenazine, raloxifene hydrochloride, loperamide hydrochloride, nonyloxytryptamine hydrochloride, paroxetine maleate, clofazimine, fluoxetine hydrochloride, toremifene citrate, amiodarone hydrochloride, saquinavir mesylate, indatraline hydrochloride, duloxetine hydrochloride, clomipramine hydrochloride, clomipramine hydrochloride, salmeterol, mefloquine hydrochloride, lofepramine, imatinib mesylate, nelfinavir mesylate, miconazole nitrate, trifluoperazine hydrochloride, sertraline hydrochloride, carvedilol, aripiprazole, azelastine hydrochloride, SB 205607 dihydrobromide, econazole nitrate, amitriptyline hydrochloride, cyproheptadine hydrochloride, benproperine phosphate, dextromethorphan hydrobromide monohydrate, rimcazole dihydrochloride, clomifene citrate, imipramine hydrochloride, naltrindole hydrochloride hydrate, prochloperazine maleate, chlorpromazine hydrochloride, haloperidol hydrochloride, hydroxyzine pamoate, diphenoxylate hydrochloride, CGS 12066B dimaleate, amoxapine, desipramine hydrochloride, olanzapine, pizotyline maleate, naftopidil, verapamil hydrochloride, clozapine, promethazine hydrochloride, SKF 83566 hydrobromide, ketoconazole, nortriptyline hydrochloride, terfenadine, indacaterol maleate, a salt thereof or combinations thereof.

12. The method of claim 10, wherein the combination results in the increased delivery of the small non-coding RNA or antisense oligonucleotide into the cytosol of the cell as compared to the delivery of the small non-coding RNA or antisense oligonucleotide alone.

* * * * *

UNITED STATES PATENT AND TRADEMARK OFFICE
CERTIFICATE OF CORRECTION

| | |
|---|---|
| PATENT NO. | : 11,033,572 B2 |
| APPLICATION NO. | : 16/479014 |
| DATED | : June 15, 2021 |
| INVENTOR(S) | : Koen Raemdonck and Stefaan De Smedt |

Page 1 of 1

It is certified that error appears in the above-identified patent and that said Letters Patent is hereby corrected as shown below:

On the Title Page

Item (74), attorney, agent, or firm, delete "Dinsmore & Shohl, LLP" and insert --Dinsmore & Shohl LLP--, therefor.

In the Specification

In Column 1, Line(s) 4, insert --CROSS REFERENCES TO RELATED APPLICATIONS
This application is a national-stage application under 35 U.S.C. § 371 of International Application No. PCT/EP2018/051220, filed January 18, 2018, which claims benefit of priority to European Patent Application No. 17152264.2, filed January 19, 2017.--.

In Column 27 & 28, row (35) Rimcazole dihydrochloride, delete " 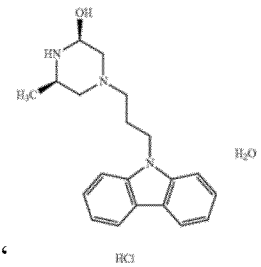 " and insert -- 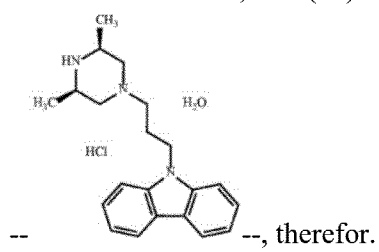 --, therefor.

In Column 54, Line(s) 46, delete "(0.6 pmol siRNA/well 2 nM siRNA)" and insert --(0.6 pmol siRNA/well ≈ 2 nM siRNA)--, therefor.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*